United States Patent
Hartnagel et al.

(10) Patent No.: US 11,813,589 B2
(45) Date of Patent: Nov. 14, 2023

(54) SUPERABSORBENT COMPLEXED WITH ALUMINUM IONS

(71) Applicant: BASF SE, Ludwigshafen (DE)

(72) Inventors: Kristine Hartnagel, Ludwigshafen (DE); Wanthip Poomsuwan, Chon Buri (TH); Patrick Neal Hamilton, Freeport, TX (US); Norbert Herfert, Shanghai (CN); Thomas Daniel, Ludwigshafen (DE); Olaf Hoeller, Charlotte, NC (US)

(73) Assignee: BASF SE, Ludwigshafen (DE)

( * ) Notice: Subject to any disclaimer, the term of this patent is extended or adjusted under 35 U.S.C. 154(b) by 518 days.

(21) Appl. No.: 16/757,523

(22) PCT Filed: Oct. 31, 2018

(86) PCT No.: PCT/EP2018/079858
§ 371 (c)(1),
(2) Date: Apr. 20, 2020

(87) PCT Pub. No.: WO2019/091848
PCT Pub. Date: May 16, 2019

(65) Prior Publication Data
US 2021/0187479 A1 Jun. 24, 2021

(30) Foreign Application Priority Data
Nov. 10, 2017 (EP) ..................... 17200963

(51) Int. Cl.
| | | |
|---|---|---|
| *B01J 20/32* | (2006.01) | |
| *A61L 15/18* | (2006.01) | |
| *A61L 15/24* | (2006.01) | |
| *A61L 15/60* | (2006.01) | |
| *B01J 20/02* | (2006.01) | |
| *B01J 20/26* | (2006.01) | |
| *B01J 20/30* | (2006.01) | |
| *C08J 3/07* | (2006.01) | |
| *C08J 3/12* | (2006.01) | |
| *C08J 3/24* | (2006.01) | |

(52) U.S. Cl.
CPC .......... *B01J 20/3236* (2013.01); *A61L 15/18* (2013.01); *A61L 15/24* (2013.01); *A61L 15/60* (2013.01); *B01J 20/0292* (2013.01); *B01J 20/267* (2013.01); *B01J 20/3021* (2013.01); *C08J 3/07* (2013.01); *C08J 3/12* (2013.01); *C08J 3/245* (2013.01); *B01J 2220/68* (2013.01); *C08J 2333/02* (2013.01)

(58) Field of Classification Search
CPC .... B01J 20/32; B01J 20/3236; B01J 20/0292; B01J 20/267; B01J 20/3021; B01J 2220/68; A61L 15/18; A61L 15/24; A61L 154/60; C08J 3/07; C08J 3/12; C08J 3/245; C08J 2333/02

USPC ........................................................ 502/402
See application file for complete search history.

(56) References Cited

U.S. PATENT DOCUMENTS

| | | | |
|---|---|---|---|
| 4,020,256 | A | 4/1977 | Zweigle et al. |
| 4,670,524 | A | 6/1987 | Messmer et al. |
| 6,150,477 | A | 11/2000 | Engelhardt et al. |
| 6,241,928 | B1 | 6/2001 | Hatsuda et al. |
| 6,620,889 | B1 | 9/2003 | Mertens et al. |
| 7,994,266 | B2 | 8/2011 | Ducker et al. |
| 2002/0193546 | A1 | 12/2002 | Freeman et al. |
| 2005/0085604 | A1 | 4/2005 | Handa et al. |
| 2005/0272600 | A1 | 12/2005 | Wada et al. |
| 2009/0275470 | A1 | 11/2009 | Nagasawa et al. |

FOREIGN PATENT DOCUMENTS

| | | |
|---|---|---|
| DE | 3519013 A1 | 11/1986 |
| DE | 38 25 366 A1 | 2/1989 |
| DE | 195 43 368 A1 | 5/1997 |
| DE | 196 46 484 A1 | 5/1997 |
| DE | 19846413 A1 | 4/2000 |
| DE | 103 31 450 A1 | 1/2005 |
| DE | 103 31 456 A1 | 2/2005 |
| DE | 103 55 401 A1 | 6/2005 |
| DE | 102005044035 A1 | 3/2007 |
| EP | 348 180 A2 | 12/1989 |
| EP | 445 619 A2 | 9/1991 |
| EP | 457 660 A1 | 11/1991 |
| EP | 530 438 A1 | 3/1993 |
| EP | 547 847 A1 | 6/1993 |
| EP | 559 476 A1 | 9/1993 |
| EP | 632 068 A1 | 1/1995 |
| EP | 668080 A2 | 8/1995 |

(Continued)

OTHER PUBLICATIONS

Buchholz et al. (eds.), Modern Superabsorbent Polymer Technology, 1st Edition, Nov. 25, 1997, 5 pages.

(Continued)

*Primary Examiner* — Edward M Johnson
(74) *Attorney, Agent, or Firm* — MARSHALL, GERSTEIN & BORUN LLP

(57) ABSTRACT

In an improved superabsorbent complexed with aluminum ions, the aluminum ions are applied in the form of an aqueous solution comprising aluminum ions, which has the feature that it comprises aluminum ions in a proportion within the range of 0.5%-15% by weight (converted if appropriate to $Al^{3+}$), based on the total mass of the solution, and further comprises anions of lactic acid (lactate ions) and phosphoric acid (phosphate ions), where the molar proportion of the lactate ions is within the range of 0.01-2.99 times the molar amount of $Al^{3+}$ and the molar proportion of the phosphate ions is within the range of 0.01-2.99 times the molar amount of $Al^{3+}$.

15 Claims, No Drawings

(56) References Cited

FOREIGN PATENT DOCUMENTS

| | | | |
|---|---|---|---|
| EP | 0781804 A2 | 7/1997 |
| EP | 816 383 A1 | 1/1998 |
| EP | 955 086 A2 | 11/1999 |
| EP | 1199315 A2 | 4/2002 |
| EP | 2112172 A1 | 10/2009 |
| EP | 2163302 A1 | 3/2010 |
| JP | H05086251 A | 4/1993 |
| WO | WO-90/15830 A1 | 12/1990 |
| WO | WO-93/21237 A1 | 10/1993 |
| WO | WO-96/40427 A1 | 12/1996 |
| WO | WO-98/48857 A1 | 11/1998 |
| WO | WO-99/18067 A1 | 4/1999 |
| WO | WO-00/55245 A1 | 9/2000 |
| WO | WO-01/38402 A1 | 5/2001 |
| WO | WO-01/74913 A1 | 10/2001 |
| WO | WO-2002/32962 A2 | 4/2002 |
| WO | WO-2002/055469 A1 | 7/2002 |
| WO | WO-02/94328 A2 | 11/2002 |
| WO | WO-02/94329 A1 | 11/2002 |
| WO | WO-2003/078378 A1 | 9/2003 |
| WO | WO-2003/104299 A1 | 12/2003 |
| WO | WO-2003/104300 A1 | 12/2003 |
| WO | WO-2003/104301 A1 | 12/2003 |
| WO | WO-2004/035514 A1 | 4/2004 |
| WO | WO-2004/084962 A1 | 10/2004 |
| WO | WO-2004/113452 A1 | 12/2004 |
| WO | WO-2005/108472 A1 | 11/2005 |
| WO | WO-2006/058682 A1 | 6/2006 |
| WO | WO-2006/109882 A1 | 10/2006 |
| WO | WO-2006/111402 A2 | 10/2006 |
| WO | WO-2007/093531 A1 | 8/2007 |
| WO | WO-2008/086976 A1 | 7/2008 |
| WO | WO-2008/092842 A1 | 8/2008 |
| WO | WO-2009/027356 A1 | 3/2009 |
| WO | WO-2009/060062 A1 | 5/2009 |
| WO | WO-2009/080611 A2 | 7/2009 |
| WO | WO-2010/012762 A2 | 2/2010 |
| WO | WO-2010/108875 A1 | 9/2010 |
| WO | WO-2011/061125 A2 | 5/2011 |
| WO | WO-2011/113777 A1 | 9/2011 |
| WO | WO-2012/045705 A1 | 4/2012 |
| WO | WO-2013/144026 A1 | 10/2013 |
| WO | WO-2013/156281 A1 | 10/2013 |
| WO | WO-2018/029045 A1 | 2/2018 |
| WO | WO-2018/141677 A1 | 8/2018 |
| WO | WO-2018/149783 A1 | 8/2018 |
| WO | WO-2019/025210 A1 | 2/2019 |
| WO | WO-2019/091848 A1 | 5/2019 |

OTHER PUBLICATIONS

International Application No. PCT/EP2018/079858, International Search Report, dated Jan. 23, 2019.

SUPERABSORBENT COMPLEXED WITH ALUMINUM IONS

CROSS-REFERENCE TO RELATED APPLICATIONS

This is the U.S. national phase of International Application No. PCT/EP2018/079858, filed Oct. 31, 2018, which claims the benefit of European Patent Application No. 17200963.1, filed Nov. 10, 2017.

The present invention relates to an improved superabsorbent, to a process for producing it and to the use thereof and to hygiene articles comprising it.

Superabsorbents are known. For such materials, names such as "highly swellable polymer", "hydrogel" (often also used for the dry form), "hydrogel-forming polymer", "water-absorbing polymer", "absorbent gel-forming material", "swellable resin", "water-absorbing resin" or the like are also commonly used. These materials are crosslinked hydrophilic polymers, more particularly polymers formed from (co)polymerized hydrophilic monomers, graft (co) polymers of one or more hydrophilic monomers on a suitable graft base, crosslinked cellulose ethers or starch ethers, crosslinked carboxymethylcellulose, partly crosslinked polyalkylene oxide or natural products swellable in aqueous liquids, for example guar derivatives, the most common being water-absorbing polymers based on partly neutralized acrylic acid. The essential properties of superabsorbents are their abilities to absorb several times their own weight of aqueous liquids and not to release the liquid again even under a certain pressure. The superabsorbent, which is used in the form of a dry powder, is converted to a gel when it absorbs fluid, and correspondingly to a hydrogel when it absorbs water as usual. Crosslinking is essential for synthetic superabsorbents and is an important difference from customary straightforward thickeners, since it leads to the insolubility of the polymers in water. Soluble substances would be unusable as superabsorbents. By far the most important field of use of superabsorbents is the absorption of body fluids. Superabsorbents are used, for example, in diapers for infants, incontinence products for adults or feminine hygiene products. Other fields of use are, for example, as water-retaining agents in market gardening, as means of water storage for protection from fire, for fluid absorption in food packaging, or quite generally for absorbing moisture.

Superabsorbents are capable of absorbing several times their own weight of water and of retaining it under a certain pressure. In general, such a superabsorbent has a CRC ("centrifuge retention capacity", see below for test method) of at least 5 g/g, preferably at least 10 g/g and more preferably at least 15 g/g. A "superabsorbent" may also be a mixture of different individual superabsorbent substances or a mixture of components which exhibit superabsorbent properties only when they interact; it is not so much the physical composition as the superabsorbent properties that are important here.

Important features for a superabsorbent are not only its absorption capacity, but also the ability to retain fluid under pressure (retention, usually expressed as "Absorption under Load" ("AUL") or "Absorption against Pressure" ("AAP"), for test method see below) and the permeability, i.e. the ability to conduct fluid in the swollen state (usually expressed as "Saline Flow Conductivity" ("SFC") or as "Gel Bed Permeability" ("GBP"), for test method see below (although changes to the superabsorbent do not necessarily alter both its SFC and GBP values, or alter them to the same degree)). Swollen gel can hinder or prevent fluid conductivity to as yet unswollen superabsorbent ("gel blocking"). Good conductivity properties for fluids are possessed, for example, by hydrogels which have a high gel strength in the swollen state. Gels with only a low gel strength are deformable under an applied pressure (body pressure), block pores in the superabsorbent/cellulose fiber absorbent core and thus prevent fluid conductivity to as yet unswollen or incompletely swollen superabsorbent and fluid absorption by this as yet unswollen or incompletely swollen superabsorbent. An increased gel strength is generally achieved through a higher degree of crosslinking, but this reduces the absorption capacity of the product. An elegant method of increasing the gel strength is that of increasing the degree of crosslinking at the surface of the superabsorbent particles compared to the interior of the particles. To this end, superabsorbent particles which have usually been dried in a surface postcrosslinking step and have an average crosslinking density are subjected to additional crosslinking in a thin surface layer of the particles thereof. The surface postcrosslinking increases the crosslinking density in the shell of the superabsorbent particles, which raises the absorption under compressive stress to a higher level. While the absorption capacity in the surface layer of the superabsorbent particles falls, their core, as a result of the presence of mobile polymer chains, has an improved absorption capacity compared to the shell, such that the shell structure ensures improved permeability, without occurrence of gel blocking. It is likewise known that superabsorbents which are relatively highly crosslinked overall can be obtained, and that the degree of crosslinking in the interior of the particles can subsequently be reduced compared to an outer shell of the particles.

Processes for producing superabsorbents are also known. Superabsorbents based on acrylic acid, which are the most common on the market, are produced by free-radical polymerization of acrylic acid in the presence of a crosslinker (the "inner crosslinker"), the acrylic acid being neutralized to a certain degree before, after or partly before and partly after the polymerization, typically by adding alkali, usually an aqueous sodium hydroxide solution. The polymer gel thus obtained is comminuted (according to the polymerization reactor used, this can be done simultaneously with the polymerization) and dried. The dry powder thus obtained (the "base polymer") is typically postcrosslinked on the surface of the particles, by reacting it with further crosslinkers, for instance organic crosslinkers or polyvalent cations, for example aluminum (usually used in the form of aluminum sulfate) or both, in order to obtain a more highly crosslinked surface layer compared to the particle interior.

A problem which often occurs in the case of superabsorbents is discoloration, which occurs in the course of storage under elevated temperature or elevated air humidity. Such conditions often occur in the case of storage of superabsorbents in tropical or subtropical countries. Superabsorbents tend to yellow under such conditions; they may even assume a brown or even almost black color. This discoloration of the actually colorless superabsorbent powder is unsightly and undesired, since it is visible especially in the desired thin hygiene products, and consumers reject unsightly hygiene products. The cause of the discoloration has not been entirely clarified, but reactive compounds such as residual monomers from the polymerization, the use of some initiators, impurities in the monomer or the neutralizing agent, surface postcrosslinkers or stabilizers in the monomers used appear to be involved.

Fredric L. Buchholz and Andrew T. Graham (publishers), in: "Modern Superabsorbent Polymer Technology", J. Wiley & Sons, New York, U.S.A./Wiley-VCH, Weinheim, Germany, 1997, ISBN 0-471-19411-5, give a comprehensive review of superabsorbents, the properties thereof and processes for producing superabsorbents.

The addition of polyvalent cations to superabsorbents in the course of surface postcrosslinking with surface postcrosslinkers which form covalent bonds between the polymer chains is known. For instance, WO 98/48 857 A1 describes superabsorbents which are crosslinked with Al, Fe, Zr, Mg or Zn cations and then mixed with a liquid such as water, mineral oil or polyols. WO 01/74 913 A1 relates to the regeneration of superabsorbents, specifically to the increase in a permeability reduced by attrition, by addition of a solution of an at least trivalent cation, typically of an aqueous aluminum sulfate solution. U.S. Pat. No. 6,620,889 B1 discloses superabsorbents which are surface postcrosslinked with a combination of a polyol and a salt of a polyvalent metal in aqueous solution. The anion of the salt may be chloride, bromide, sulfate, carbonate, nitrate, phosphate, acetate or lactate. The use of aluminum sulfate is preferred.

According to the teaching of WO 2006/111 402 A2, a base polymer is treated with a permeability improver selected from silicon-oxygen compounds, salts of polyvalent, especially trivalent, cations or mixtures thereof. The salt of a trivalent cation is preferably an aluminum salt, which is selected from a group of salts including aluminum lactate, oxalate, citrate, glyoxylate, succinate, tartrate and other organic and inorganic aluminum salts. WO 2005/108 472 A1 discloses a process which comprises the treatment of a base polymer with a water-soluble salt of a polyvalent metal and an organic acid or salt thereof. The salt of a polyvalent metal is preferably aluminum sulfate. The organic acid or salt thereof is selected from a group of acids including citric acid, glyoxylic acid, glutaric acid, succinic acid, tartaric acid, lactic acid and the alkali metal or ammonium salts of these acids.

WO 2004/113 452 A1 describes superabsorbents which are treated with concentrated solutions of polyvalent metal salts, especially sodium aluminate. WO 2013/156 281 A1 teaches the treatment of superabsorbents with aluminum glycinate. WO 2010/108 875 A1, WO 2012/045 705 A1 and WO 2013/156 330 A1 teach the treatment of superabsorbents with basic aluminum salts such as basic aluminum acetate or aluminum lactate.

WO 2009/080 611 A2 discloses the treatment of superabsorbents with mixtures of aluminum salts, one of which comprises a chelating anion, for example dicarboxylates or hydroxycarboxylates, particular preference being given to lactate, and the other a weakly complexing anion, for example chloride, nitrate, sulfate, hydrogensulfate, carbonate, hydrogencarbonate, nitrate, phosphate, hydrogenphosphate, dihydrogenphosphate or carboxylate, particular preference being given to sulfate.

The exact form in which the anions used in the aluminum salts are ultimately present on the superabsorbent is unknown. In other words, the exact structure of the aluminum complexes formed on the particle surfaces is unknown. However, it is known from the prior art that the anions used in the aluminum salts affect the properties of the superabsorbent. One problem with the use of particular anions or particular anion mixtures is the solubility thereof in the usually aqueous aluminum salt solution which is applied to the superabsorbent. If compounds precipitate out there, i.e. if the solution is unstable, according to the circumstances of the addition, especially the age and temperature of the solution, the result is inhomogeneous superabsorbents, and aluminum is withdrawn as a solid precipitate from the complexation of carboxylate groups at the surface of the superabsorbent particles, such that the desired permeability-enhancing effect only occurs to a reduced degree, if at all. For example, because of the low solubility of aluminum phosphate, phosphate has to date been an anion usable only with difficulty in the complexation of superabsorbents with aluminum. There may be reasons to admix a superabsorbent with solid or suspended aluminum phosphate powder, but this is not surface complexation in the interests of higher permeability.

For stabilization of superabsorbents to discoloration, a reducing agent is often added. WO 00/55 245 A1 teaches the stabilization of superabsorbents against discoloration by treatment with an inorganic reducing agent and optionally a metal salt, for instance an alkaline earth metal salt, which is added after the polymerization. The inorganic reducing agent is typically a hypophosphite, phosphite, bisulfite or sulfite. The metal salt is typically a colorless (the property of "colorless" is often also simply referred to as "white") phosphate, acetate or lactate, but not a halide. According to the teaching of WO 2006/058 682 A1, discoloration of superabsorbents is avoided when the drying and the postcrosslinking reaction are carried out in an atmosphere which is essentially free of oxidizing gases. WO 2009/060 062 A1 or WO 2010/012 762 A2 teach the addition of sulfinic acid derivatives to superabsorbents in order to stabilize them against discoloration. EP 1 199 315 A2 teaches the use of a redox initiator system for initiating a polymerization reaction, said redox initiator system comprising, as the reducing component, a sulfinic acid or a sulfinate, especially 2-hydroxysulfinatoacetic acid or a salt thereof. WO 99/18 067 A1 discloses particular hydroxyl- or aminoalkyl- or arylsulfinic acid derivatives or mixtures thereof and the use thereof as reducing agents which do not release formaldehyde. WO 2004/084 962 A1 relates to the use of these sulfinic acid derivatives as the reducing component of a redox initiator for polymerization of partly neutralized acrylic acid to superabsorbents.

Published specification JP 05/086 251 teaches the use of phosphoric acid derivatives or salts thereof, especially (1-hydroxyethane-1,1-diyl)bisphosphonic acid (also "1-hydroxyethylidene-1,1-diphosphonic acid", "1-hydroxyethane-(1,1-diphosphonic acid)", trivial name "etidronic acid"), ethylenediaminetetra(methylenephosphonic acid), diethylenetriaminepenta(methylenephosphonic acid) or the alkali metal or ammonium salts thereof as stabilizers of superabsorbents against discoloration. EP 781 804 A2 teaches, for the same purpose, the addition of (1-hydroxyalkyl-1,1-diyl)bisphosphonic acids, the alkyl radical comprising from 5 up to 23 carbon atoms.

EP 668 080 A2 teaches the addition of inorganic acids, organic acids or polyamino acids to superabsorbents, the inorganic acids specified also including phosphorus-based acids. US 2005/0 085 604 A1 discloses the addition of chelating agents and oxidizing or reducing agents to superabsorbents, the chelating agents also including those containing phosphorus. US 2005/0 272 600 A1 relates to the addition of ion blockers to superabsorbents, which also include organic phosphorus compounds. (1 Hydroxyethane-1,1-diyl)bisphosphonic acid is one of the examples mentioned. According to the teaching of EP 2 112 172 A1, an organic phosphorus compound is added to the monomer solution which is polymerized to give the superabsorbent; (1-hydroxyethane-1,1-diyl)bisphosphonic acid is mentioned; ethylenediaminetetra(methylenephosphonic acid) is the most preferred compound. US 2009/0 275 470 A1 teaches adding both chelating agents and preferably inorganic phosphorus compounds to superabsorbents, and the chelating agents may also be a phosphorus compound, for example (1-hydroxyethane-1,1-diyl)bisphosphonic acid or ethylenediaminetetra(methylenephosphonic acid). According to the teaching of WO 2006/109 882 A1 too, such compounds are also added to superabsorbents as chelating agents, with use not only of phosphorus compounds but also of sulfur-containing reducing agents in various process stages. WO 2013/144 026 A1 teaches superabsorbents coated with aluminum ions and etidronic acid that are in a particular molar ratio.

It is therefore a constant objective to find other or even improved superabsorbents, especially those which are both permeable and stabilized against discoloration, especially to yellowing or browning in the course of storage under elevated temperature and/or elevated air humidity, and processes for production thereof. These superabsorbents should also be producible without precipitation problems in the complexation with aluminum ions, especially in the presence of phosphate ions. There should be no, or at least no significant, accompanying impairment of the use properties of the superabsorbent, especially its absorption capacity for fluid, including under pressure. Further objects of the invention are uses of this superabsorbent, such as hygiene products comprising this superabsorbent and processes for production thereof.

This object was achieved by a superabsorbent complexed with aluminum ions, where the aluminum ions are applied in the form of an aqueous solution comprising aluminum ions, which has the feature that it comprises aluminum ions in a proportion within the range of 0.5%-15% by weight (converted if appropriate to $Al^{3+}$), based on the total mass of the solution, and further comprises anions of lactic acid (lactate ions) and phosphoric acid (phosphate ions), where the molar proportion of the lactate ions is within the range of 0.01-2.99 times the molar amount of $Al^{3+}$ and the molar proportion of the phosphate ions is within the range of 0.01-2.99 times the molar amount of $Al^{3+}$.

Proportions for the charged ions specified are based in each case on the ions themselves, and so, for example, proportions determined as oxides (e.g. $Al_2O_3$) or converted thereto should be converted to the ions.

A process for producing the superabsorbent of the invention has also been found, namely by polymerizing an aqueous monomer solution comprising a) at least one ethylenically unsaturated monomer which bears acid groups and is optionally at least partly in salt form,
b) at least one crosslinker,
c) at least one initiator,
d) optionally one or more ethylenically unsaturated monomers copolymerizable with the monomers mentioned under a),
e) optionally one or more water-soluble polymers,
the process further comprising
drying of the resulting polymer,
optionally grinding of the dried polymer and sieving of the ground polymer,
optionally surface postcrosslinking of the dried and optionally ground and sieved polymer, and
adding an aqueous solution comprising aluminum ions, which has the feature that it comprises aluminum ions in a proportion within the range of 0.5%-15% by weight (converted if appropriate to $Al^{3+}$), based on the total mass of the solution, and further comprises anions of lactic acid (lactate ions) and phosphoric acid (phosphate ions), where the molar proportion of the lactate ions is within the range of 0.01-2.99 times the molar amount of $Al^{3+}$ and the molar proportion of the phosphate ions is within the range of 0.01-2.99 times the molar amount of $Al^{3+}$.

The superabsorbents of the invention surprisingly exhibit good permeability and stability against discoloration, without any significant impairment in their other use properties such as CRC or AUL. By virtue of the lactate present in addition to aluminum ions and phosphate ions, it is possible to obtain a stable solution.

In addition to lactate and phosphate, it is also possible for other anions to be present in the solution to be used in accordance with the invention. However, the presence of lactate appears to be advantageous or even absolutely necessary for the stabilization of the aluminum- and phosphate-containing solution. A stable solution which is lactate-free but comprises aluminum ions and phosphate ions, in particular, also seems to be obtainable in the form of a solution comprising aluminum ions, phosphate ions and sulfate ions. However, the sulfate component reduces stability to discoloration. Preferably, therefore, the solution comprising aluminum ions to be used in accordance with the invention comprises not more than 5% by weight of sulfate ions, preferably not more than 3% by weight of sulfate ions and more preferably not more than 1% by weight of sulfate ions. In a very particularly preferred manner, the solution is sulfate-free, i.e. free of deliberately added sulfate.

Articles for absorption of fluids have additionally been found, especially hygiene articles for absorption of fluid excretions or fluid components of excretions, which comprise the superabsorbent of the invention. Processes for production of such articles for absorption of fluids have also been found, the production of these articles involving addition of the superabsorbent of the invention thereto.

The surfaces of the superabsorbent of the invention have been complexed with aluminum ions. Superabsorbents are very predominantly produced in the form of powders; in most cases, complexation of the surfaces thereof thus means complexation of the particle surfaces. Some superabsorbents are also produced in other forms, for example as foams, fibers, roll material, or as superabsorbent particles fixed on a carrier, for instance a nonwoven web. The surfaces of such superabsorbents may also be complexed with aluminum. The complexation of the surface of superabsorbents is known per se. "Complexation" is, strictly speaking, solely a specific term for the special case of surface postcrosslinking in which aluminum ions form ionic bonds between several polar groups at the surface of the superabsorbent particles. The complexation is often also discussed as part of "surface postcrosslinking". In the context of this invention, "complexation" is understood to mean surface postcrosslinking with aluminum ions, in order to delimit it from surface postcrosslinking with postcrosslinkers which form covalent bonds with polar groups at the surface of the superabsorbent particles.

Aluminum ions are generally added to the superabsorbent in the complexation in an amount of at least 0.008% by weight, preferably at least 0.015% by weight and more preferably at least 0.020% by weight, and generally at most 0.15% by weight, preferably at most 0.10% by weight and more preferably at most 0.05% by weight, in each case calculated as the metal (or $Al^{3+}$ ion) and based on the total amount of the anhydrous superabsorbent.

In a preferred embodiment, the aqueous solution used in accordance with the invention may further comprise an anion of at least one third acid, where the third acid is preferably selected from a group comprising amino acids, carboxylic acids, citric acid, tartaric acid, malic acid, oxalic acid, glycolic acid, succinic acid, gluconic acid, glycine, acetic acid, sulfuric acid and/or combinations. Charges that have not been balanced out by lactate, acid anion (from the third acid) and phosphate can be balanced out, for example, by $OH^-$ ions.

In a preferred embodiment, as well as aluminum, it is also possible for one further type of cation or multiple further types of cation to be present in the solution. The amount and number of different cations among these exceeds that of the cations that are present as an impurity in any case—especially in the case of use of substances in technical grade quality. Therefore, a further cation shall refer hereinafter to any deliberate or desired addition of cations. Particularly preferred cations have been found to be alkali metal and alkaline earth metal ions. These are an option especially because they usually form readily soluble salts and are therefore firstly readily soluble, and secondly also rarely have a tendency to precipitate out of an Al-containing solution. Alternatively or additionally to these cations, cations of the transition metals or rare earth metals are also possible as cationic additions. In a particularly preferred embodiment, the added cation is an ammonium ion. Alternatively or additionally, $Na^+$, $K^+$, $Ca^{2+}$, $Mg^{2+}$ or $Zr^{4+}$ have been found to be useful as cationic additions in aluminum lactate phosphate solutions. In a preferred embodiment, it is a feature of the aqueous solution that it comprises an addition of a cation, where the cation is preferably selected from a group comprising alkali metal ions, alkaline earth metal ions, ammonium ions, cations of one or more transition metals or rare earth metals, and combinations of these. In a particularly preferred embodiment, an added cation is selected from the group comprising $Na^+$, $K^+$, $Ca^{2+}$, $Mg^{2+}$, $Zr^{4+}$, $NH_4^+$ or combinations thereof.

In a further preferred embodiment, the solution includes clusters having the theoretical composition $Al^{3+}{}_A(C_3H_5O_3^-)_{x \cdot A} S^{M-}{}_{y \cdot A}(H_2PO_4^-)_{z \cdot A}(OH^-)_{(3A-x \cdot A-M \cdot y \cdot A-z \cdot A)}$ where S is the anion of an optionally present third acid having charge M, x is a value within the range of 0.01-2.99, preferably 0.5-2.8, further preferably 0.75-2.0, most preferably 1.0-1.5, y is a value within the range of 0-2.8, preferably 0-2, preferably 0-1.25, more preferably 0-1.0, and z is a value within the range of 0.05-2.9, preferably 0.1-2.5, further preferably 0.2-1.5, more preferably 0.3-1.25. The sum of x, M.y and z is preferably ≤3, such that, according to the above formula, the positive charge of the aluminum ions is balanced out. However, other cations (described in detail hereinafter) are also conceivable in the solution, such that the sum total of x, M.y and z may also be greater than 3. Since lactate and phosphate are necessarily present in order to be able to obtain a stable aluminum- and phosphate-containing solution, x and z are always >0.

Lactate ions are preferably, but not absolutely necessarily, the most commonly occurring anionic component in the solution—based on the molar proportion of the dissolved substances. As apparent from the above formula, x in the clusters may assume a value in the range of 0.5-2.8, such that, in the case of a factor of 2.8, a majority of the charge introduced into the solution by the aluminum ions has already been compensated for by lactate ions. The proportion of phosphate ions is therefore then correspondingly small. Further charges introduced by aluminum cations can be compensated for by the additional acid S or the optionally present $OH^-$ ions.

In a preferred embodiment, Y>0. Thus, according to the abovementioned formula, at least one anion of a third acid is present. Preferably, this acid or its anion is selected from a group comprising amino acids, carboxylic acids, citrate, tartrate, malate, oxalate, glycolate, succinate, gluconate, glycinate, acetate, sulfate and/or combinations thereof. Studies have shown that these anions can further enhance the stability of the aqueous solution. Moreover, in some cases, an increase in the concentration of aluminum ions and/or phosphate ions is possible.

In a preferred embodiment, it is a feature of the aqueous solution that it is stable within a temperature range of 0-80° C. Particular preference is given to aqueous solutions which are storage-stable even at low temperatures. Preference is given to solutions that are storage-stable at <30° C., preferably <20° C., more preferably <10° C. "Storage-stable" shall be understood to mean stability over periods exceeding preferably 1 month, preferably 6 months, more preferably 12 months. Thus, an aqueous solution is preferably storage-stable for longer than 1 month, preferably longer 6 months, more preferably longer than 12 months. This storage stability permits storage and/or transportation of these solutions until they are used. Transport over long distances, for example by truck or even by ship, is also possible given such storage stability.

In order to maximize the phosphate content of the solution, it is preferable that a maximum proportion of the anions are phosphate ions. According to the above formula, x is thus preferably comparatively small. In a preferred embodiment of the present invention, x is within a range of 0.5-2.5, preferably within a range of 0.75-2.0, more preferably in the range between 1.0 and 1.5. In the range from x=1.0 to x=1.5, one third to half of the positive charges introduced into the solution by the triply positively charged aluminum cations is thus compensated for by lactate. The rest of the negative charge needed for compensation for the positive charge can be provided by anions S from the acid, phosphate ions or $OH^-$ ions. The stability of the solution decreases at a value of x of <0.5. It seems to be the case that, with low lactate contents, the stabilization of the solution is inadequate and there can therefore be precipitation of aluminum phosphate, depending on the storage conditions.

It is also true in respect of the amount of anions from the additional third acid (S) that this should be at a minimum in order to be able to maximize the phosphate content. In a preferred embodiment, Y is therefore less than 1.25, preferably less than 1.0, more preferably less than 0.8.

In a preferred embodiment, the third acid has an additional functionality. Such an additional functionality is more preferably selected from a group comprising substituents that introduce an amino function, a further acid function, a carbonyl function, a double bond, a triple bond, a heteroatom, a charge, a partial charge and/or combinations thereof into the molecule. Especially when the functionality of the third acid is capable of positively altering the properties of the desired solution, the proportion of the third acid can be very high and can even exceed, for example, the proportion of phosphoric acid and/or lactic acid. Especially when the establishment of a particular pH is desired, this can be achieved in some preferred embodiments through the selection of a suitable third acid which incorporates appropriate functionalities. For example, it would also be possible to achieve a buffer function, for example by means of an amino function and or a (further) acid function. It would thus be possible to keep the pH at least substantially constant even in the event of alteration of the ambient conditions (e.g. temperature variations, impurities, dilutions (for example by rainwater)) and to avoid the precipitation of salts and/or other solids.

It has been found that it is advantageous especially for long-term storage stability when X>Z. In a preferred embodiment, the proportion of lactate ions in the solution is thus greater than that of the phosphate ions. However, as shown below, this is not absolutely necessary.

In order to assure the long-term stability of the solution, it is preferable that the concentration of the aluminum ions is within the range of 1%-10% by weight (converted if appropriate to $Al^{3+}$), based on the total mass of the solution. Further preferably, the concentration of the aluminum ions (converted if appropriate to $Al^{3+}$) is within the range of 1.5%-5% by weight.

In a further preferred embodiment, it is a feature of the aqueous solution that, in the theatrical composition $Al^{3+}{}_A(C_3H_5O_3^-)_{x.A}S^{M-}{}_{y.A}(H_2PO_4^-)_{z.A}(OH^-)_{(3A-x.A-M.y.A-z.A)}$ of the dissolved substances, the index (3A-x.A-M.y.A-z.A) is >0. Thus, there are preferably OH$^-$ ions present. It is more preferable that the index (3A-x.A-M.y.A-z.A) is within the range from 0.5 to about 1.75 (see examples below). The sum of x, M.y and z is thus preferably in the range of 1.25 to 2.5.

It is possible for further stabilizers (for example chelating agents, polymers) to be added to the solution, for example the addition of one or more substances independently selected from a group comprising acetylacetone (acac), ethylenediamine (en), 2-(2-aminoethylamino)ethanol (AEEA), diethylenetriamine (dien), iminodiacetate (ida), triethylenetetramine (trien, TETA), triaminotriethylamine (tren), nitrilotriacetate (nta), bis(salicylidene)ethylenediamine (salen), ethylenediaminotriacetate (ted), ethylenediaminetetraacetate (EDTA), diethylenetriaminepentaacetate (DTPA), 1,4,7,10-tetraazacyclododecane-1,4,7,10-tetraacetate (DOTA), dimethyl glyoxime (dmg), 8-hydroxyquinoline (oxin), 2,2'-bipyridine (bpy), 1,10-phenanthroline (phen), dimercaptosuccinic acid (DMSA), 1,2-bis(diphenylphosphino)ethane (dppe) inter alia. Especially preferred are chelating agents where at least one energetically positive interaction between the chelating agent and the cation to be complexed is formed by a heteroatoms selected from a group comprising N, P and S, or a functional group which comprises an oxygen atom and is selected from a group comprising ketones (A(C=O)B with A, B=organic radical), aldehydes (A=H, B=organic radical or H), esters (A=O—R, B=organic radical or H), amides (A=NH$_2$, NHR, NR$^1$R$^2$, B=organic radical or H), ureas (A, B=NH$_2$, NHR, NR$^1$R$^2$), urethanes (A=OR, B=NH$_2$, NHR, NR$^1$R$^2$), alcohols (A-OH, A=organic radical). However, it is preferable that the solution does not comprise any further stabilizers. It is especially preferable that the solution does not comprise any of the aforementioned stabilizers and, in particular, any of the abovementioned chelating agents.

The aluminum solutions to be used in accordance with the invention are produced, for example, by a process featuring the steps of
 a) providing water in a reaction vessel,
 b) adding a basic aluminum salt preferably selected from a group comprising aluminum carbonate, aluminum hydroxide, aluminum oxide, an aluminate and combinations thereof to the reaction vessel while stirring,
 c) adding lactic acid and/or a lactate and, in parallel or with a time delay, phosphoric acid and/or a phosphate,
 d) stirring the resultant mixture,
 where the sequence of execution of steps b) and c) is as desired.

It has been found that a stable solution can be obtained with the abovementioned sequence of the individual process steps. This process enables the production of large amounts of a desired solution, preferably as described above. For example, it is thus possible to produce more than 1 m$^3$ of the solution described above in one batch.

In a specific embodiment of the above sequence a) to d), for preparation of such a solution, aluminum is initially charged in the form of a basic salt (carbonate, hydroxide, oxide, eliminate, preferably hydroxide) in aqueous suspension with solids content 10%-20% by weight. A suitable feedstock is, for instance, the amorphous "aluminum oxide hydrates" which arise in a known manner on precipitation from aluminum salt solutions by addition of base. The use of crystalline aluminium hydroxides, for instance bayerite (alpha-Al(OH)$_3$), hydrargillite (gamma-Al(OH)$_3$), boehmite (alpha-AlO(OH)) or diaspore (gamma-AlO(OH)), is not ruled out, but is less preferred because these aluminum salts are typically slower to dissolve in acids than amorphous aluminium hydroxide or aluminum oxide hydrate. The most reactive form is naturally freshly precipitated aluminum hydroxide or aluminum oxide hydrate, but the commercially available aluminium hydroxides or aluminum oxide hydrates are also of good suitability. One example of a suitable raw material is aluminum oxide, hydrated (powder, according to Ph. Eur. 9. Ed., 47.0%-60.0% Al$_2$O$_3$, Dr. Paul Lohmann GmbH KG, article number 511066100). Subsequently, lactic acid and phosphoric acid are added while stirring and reacted at a temperature of somewhat above 40° C. This forms a clear to slightly turbid solution which is freed of any (undissolved or precipitated) solid components present by means of filtration.

If the presence of a further anionic component is envisaged, this is preferably added in the form of an acid or a readily soluble salt. Further preferably, the addition is effected together with the other substances mentioned in step c) or during or after step d).

In a preferred variant of the process, it is the case that clusters having the theoretical composition $Al^{3+}{}_A(C_3H_5O_3^-)_{x.A}S^{M-}{}_{y.A}(H_2PO_4^-)_{z.A}(OH^-)_{(3A-x.A-M.y.A-z.A)}$ are produced, where S is the anion of an optionally present third acid having charge M, x is a value within the range of 0.01-2.99, preferably 0.5-2.8, further preferably 0.75-2.0, most preferably 1.0-1.5, y is a value within the range of 0-2.8, preferably 0-2, preferably 0-1.25, more preferably 0-1.0, and z is a value within the range of 0.05-2.9, preferably 0.1-2.5, further preferably 0.2-1.5, more preferably 0.3-1.25.

More particularly, it is preferable in terms of the process that step c) is effected at a temperature of >25° C., preferably >40° C., further preferably >50° C., more preferably at 60-70° C., or alternatively under reflux. At these temperatures, the mixture or solution is supplied with sufficient energy to substantially prevent precipitation of aluminum phosphate. It is suspected that sufficient thermal energy is available at these temperatures, so that the ions can form clusters. These clusters are soluble and/or remain in colloidal form in the solution and do not precipitate out even when the temperature goes below the abovementioned temperature.

In the case of some compositions and/or variants of the process, it is not entirely impossible that a small proportion of the aluminum and/or phosphate used will precipitate out, for example, as aluminum phosphate or else together with other substances. Impurities in the starting materials may also be present as insoluble constituents in the solution or mixture. In this case, filtration is advantageous. In a preferred process variant, it is therefore a feature of the process that step c) is followed by a filtration. Preferably, this is conducted by a filtration in a filter press. The product obtained from this filtration step is a clear solution that meets the demands in relation to the desired stability and content of aluminum and phosphate ions.

The solution thus prepared is used for complexation of the superabsorbent with aluminum ions.

In addition to the complexation, the superabsorbent of the invention is preferably also surface postcrosslinked with postcrosslinkers which form covalent bonds with polar groups at the surface of the superabsorbent particles.

The superabsorbents of the invention are obtainable, for example, by the process of the invention. However, it is likewise possible to complex even superabsorbents that have not been obtained by the solution polymerization described with the aluminum solution to be used in accordance with the invention.

The process of the invention for producing superabsorbents is a process for aqueous solution polymerization of a monomer mixture comprising the following:
- a) at least one ethylenically unsaturated monomer which bears at least one acid group and is optionally at least partly in salt form,
- b) at least one crosslinker,
- c) at least one initiator,
- d) optionally one or more ethylenically unsaturated monomers copolymerizable with the monomers mentioned under a), and
- e) optionally one or more water-soluble polymers.

The monomers a) are preferably water-soluble, i.e. their solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids or salts thereof, such as acrylic acid, methacrylic acid, maleic acid or salts thereof, maleic anhydride and itaconic acid or salts thereof. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, an acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomer solution comprises preferably at most 250 ppm by weight, preferably at most 130 ppm by weight, more preferably at most 70 ppm by weight and preferably at least 10 ppm by weight, more preferably at least 30 ppm by weight, especially around 50 ppm by weight, of hydroquinone monoether, based in each case on the unneutralized monomer a); neutralized monomer a), i.e. a salt of the monomer a), is considered for arithmetic purposes to be unneutralized monomer. For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 530 438 A1, di- and triacrylates, as described in EP 547 847 A1, EP 559 476 A1, EP 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/32962 A2.

Preferred crosslinkers b) are pentaerythrityl triallyl ether, tetraallyloxyethane, methylenebismethacrylamide, 15- to 20-tuply ethoxylated trimethylolpropane triacrylate, 15-20-tuply ethoxylated glyceryl triacrylate, polyethylene glycol diacrylate having between 4 and 45 —CH$_2$CH$_2$O units in the molecule chain, trimethylolpropane triacrylate and triallylamine.

Very particularly preferred crosslinkers b) are the polyethoxylated and/or propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05% to 1.5% by weight, more preferably 0.1% to 1% by weight, most preferably 0.3% to 0.6% by weight, based in each case on monomer a). With rising crosslinker content, there is a fall in the centrifuge retention capacity (CRC) and a rise in the absorption under load (AUL).

The initiators c) used may be all compounds which generate free radicals under the polymerization conditions, for example thermal initiators, redox initiators and/or photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. However, the reducing component used is preferably also a sulfonic acid derivative, for example a mixture of the sodium salt of 2-hydroxy-2-sulfinatoacetic acid, the disodium salt of 2-hydroxy-2-sulfonatoacetic acid and sodium bisulfite, obtainable, for example, from L. Bruggemann KG (Salzstrasse 131, 74076 Heilbronn, Germany, www.brueggemann.com) under the BRUGGOLIT® FF6M or BRUGGOLIT® FF7, or alternatively BRÜGGOLITE® FF6M or BRÜGGOLITE® FF7 names, or the disodium salt of 2-hydroxy-2-sulfonatoacetic acid, obtainable, for example, from L. Bruggemann KG under the BLANCOLEN® HP name. The initiators are, incidentally, used in customary amounts. The customary amount of the reducing component of a redox initiator is generally at least 0.00001% by weight, preferably at least 0.0001% by weight and more preferably at least 0.001% by weight, and generally at most 0.2% by weight and preferably at most 0.1% by weight, based in each case on the amount of monomers a) and d). If, however, the sole reducing component used in the redox initiator is sulfonic acid derivative, the added amount thereof is generally at least 0.001% by weight, preferably at least 0.01% by weight and more preferably at least 0.03% by weight, and generally at most 1.0% by weight, preferably at most 0.3% by weight and more preferably at most 0.2% by weight, based in each case on the amount of monomers a) and d). The customary amount of the oxidizing component of a redox initiator is generally 0.0001% by weight and more preferably at least 0.001% by weight, and generally at most 2% by weight and preferably at most 1.0% by weight, based in each case on the amount of monomers a) and d). The customary amount of the thermal initiators is generally 0.01% by weight and more preferably at least 0.1% by weight, and generally at most 2% by weight and preferably at most 1.0% by weight, based in each case on the amount of monomers a) and d). The customary amount of the photoinitiators is generally 0.001% by weight and more preferably at least 0.01% by weight, and generally at most 1.0% by weight and preferably at most 0.2% by weight, based in each case on the amount of monomers a) and d).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl acrylate, dimethylaminoethyl acrylate, dimethylaminopropyl acrylate, diethylaminopropyl acrylate, dimethylaminoethyl methacrylate, diethylaminoethyl methacrylate, maleic acid or salts thereof and maleic anhydride.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40% to 75% by weight, more preferably from 45% to 70% by weight and most preferably from 50% to 65% by weight. It is also possible to use monomer suspensions, i.e. oversaturated monomer solutions. As the water content rises, the energy expenditure in the subsequent drying rises and, as the water content falls, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

The monomer mixture may comprise further components. Examples of further components used in such monomer mixtures are, for instance, chelating agents in order to keep metal ions in solution, or inorganic powders in order to increase the stiffness of the superabsorbent in the swollen state, or recycled undersize from a later grinding operation. It is possible here to use all known additions to the monomer mixture. Even though only "solution" is discussed here in connection with the monomer mixture, this also means the polymerization of a suspension, for instance when insoluble constituents are added to the monomer mixture.

The acid groups of the polymer gels resulting from the polymerization have typically been partly neutralized. Neutralization is preferably carried out at the monomer stage; in other words, salts of the monomers bearing acid groups or, to be precise, a mixture of monomers bearing acid groups and salts of the monomers bearing acid groups ("partly neutralized acid") are used as component a) in the polymerization. This is typically accomplished by mixing the neutralizing agent as an aqueous solution or preferably also as a solid into the monomer mixture intended for polymerization or preferably into the monomer bearing acid groups or a solution thereof. The degree of neutralization is preferably from 25 to 95 mol %, more preferably from 50 to 80 mol % and most preferably from 65 to 72 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably 10 to 30 mol % and more preferably 15 to 25 mol % of the acid groups before the polymerization by adding a portion of the neutralizing agent directly to the monomer solution and setting the desired final degree of neutralization only after the polymerization, at the polymer gel stage. When the polymer gel is at least partly neutralized after the polymerization, the polymer gel is preferably comminuted mechanically, for example by means of an extruder, in which case the neutralizing agent can be sprayed, sprinkled or poured on and then carefully mixed in. For this purpose, the gel material obtained can be extruded several times more for homogenization.

However, preference is given to performing the neutralization at the monomer stage. In other words: in a very particularly preferred embodiment, the monomer a) used is a mixture of 25 to 95 mol %, more preferably from 50 to 80 mol % and most preferably from 65 to 75 mol % of salt of the monomer bearing acid groups, and the remainder to 100 mol % of monomer bearing acid groups. This mixture is, for example, a mixture of sodium acrylate and acrylic acid or a mixture of potassium acrylate and acrylic acid.

In a preferred embodiment, the neutralizing agent used for the neutralization is one whose iron content is generally below 10 ppm by weight, preferably below 2 ppm by weight and more preferably below 1 ppm by weight. Likewise desired is a low content of chloride and anions of oxygen acids of chlorine. A suitable neutralizing agent is, for example, the 50% by weight sodium hydroxide solution or potassium hydroxide solution which is typically traded as "membrane grade"; even more pure and likewise suitable, but also more expensive, is the 50% by weight sodium hydroxide solution or potassium hydroxide solution typically traded as "amalgam grade" or "mercury process".

Processes for production of superabsorbents from monomer mixtures, such as those described by way of example above, are known in principle. Suitable polymerization reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/38402 A1. Polymerization on a belt is described, for example, in EP 955 086 A2, DE 38 25 366 A1 and U.S. Pat. No. 6,241,928. Polymerization in a belt reactor forms, like the likewise known polymerization in batchwise operation or in a tubular reactor, as described, for example, in EP 445 619 A2 and DE 19 846 413 A1, a polymer gel which has to be comminuted in a further process step, for example in a meat grinder, extruder or kneader. It is also possible to produce spherical or differently shaped superabsorbent particles by suspension or emulsion polymerization, as described, for example, in EP 457 660 A1, or by spray or droplet polymerization processes, as described, for example, in EP 348 180 A1, EP 816 383 A1, WO 96/404 27 A1, U.S. Pat. No. 4,020,256, US 2002/0 193 546 A1, DE 35 19 013 A1, DE 10 2005 044 035 A1, WO 2007/093531 A1, WO 2008/086 976 A1 or WO 2009/027 356 A1. Likewise known are processes in which the monomer mixture is applied to a substrate, for example a nonwoven web, and polymerized, as described, for instance, in WO 02/94 328 A2 and WO 02/94 329 A1.

It is optionally possible in a known manner to add a sulfonic acid derivative, including in a mixture with sulfite or sulfinic acid derivative, to the superabsorbent or else to the monomer mixture before or after drying, but preferably before drying. These mixtures are standard commercial products and are available, for example, in the form of mixtures of the sodium salt of 2-hydroxy-2-sulfinatoacetic acid, the disodium salt of 2-hydroxy-2-sulfonatoacetic acid and sodium bisulfite from L. Bruggemann KG (Salzstrasse 131, 74076 Heilbronn, Germany, www.brueggemann.com) under the BRUGGOLIT® FF6M or BRUGGOLIT® FF7 names, or alternatively BRUGGOLITE® FF6M or BRUGGOLITE® FF7. Preference is given to the use of the sulfonic acid derivatives in pure form. These too are standard commercial products. For example, the disodium salt of 2-hydroxy-2-sulfonatoacetic acid is available from L. Bruggemann KG (Salzstrasse 131, 74076 Heilbronn, Germany, www.brueggemann.com) under the BLANCOLEN® HP name.

The sulfonic acid derivative is generally used in an amount of at least 0.0001% by weight, preferably at least 0.001% by weight and more preferably at least 0.025% by weight, for example at least 0.05% by weight or at least 0.1% by weight, and generally at most 3% by weight, preferably at most 2% by weight and more preferably at most 0.5% by weight, for example at most 0.35% by weight or 0.2% by weight, based in each case on the total weight of the superabsorbent.

Just like the sulfonic acid derivative, it is optionally also possible in a known manner, in addition thereto or on its own, to add at least one phosphonic acid derivative to the superabsorbent or else to the monomer mixture before or after drying, but preferably before drying. Particular preference is given to the addition of preferably (1-hydroxyethane-1,1-diyl)bisphosphonic acid ("etidronic acid") or a salt thereof, especially the sodium salt, the potassium salt, the disodium salt, the dipotassium salt or the sodium potassium salt. Phosphonic acid derivatives of this kind are standard commercial products and are available, for example, under the Cublen® brand from Zschimmer & Schwarz Mohsdorf GmbH & Co KG, Chemnitztalstrasse 1, 09217 Burgstädt, Germany.

The phosphonic acid derivative is generally added in an amount of at least 0.01% by weight, preferably at least 0.1% by weight and more preferably at least 0.2% by weight, and generally at most 1.9% by weight, preferably at most 1.3% by weight and more preferably at most 0.6% by weight, based in each case on the total amount of the anhydrous superabsorbent.

The polymer gel obtained from the aqueous solution polymerization and optional subsequent neutralization is then preferably dried with a belt drier until the residual moisture content is preferably 0.5 to 15% by weight, more preferably 1 to 10% by weight and most preferably 2 to 8% by weight (see below for test method for the residual moisture or water content). In the case of too high a residual moisture content, the dried polymer gel has too low a glass transition temperature Tg and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the gel before drying is generally from 25 to 90% by weight, preferably from 30 to 80% by weight, more preferably from 35 to 70% by weight and most preferably from 40 to 60% by weight. Optionally, however, it is also possible to dry using a fluidized bed drier or a heatable mixer with a mechanical mixing unit, for example a paddle drier or a similar drier with mixing tools of different design. Optionally, the drier can be operated under nitrogen or another nonoxidizing inert gas or at least under reduced partial oxygen pressure in order to prevent oxidative yellowing processes. As a rule, however, sufficient aeration and removal of the steam will also lead to an acceptable product. In general, a minimum drying time is advantageous with regard to color and product quality.

During the drying, the residual monomer content in the polymer particles is also reduced, and last residues of the initiator are destroyed.

Thereafter, the dried polymer gel is optionally—and preferably—ground and classified, in which case the apparatus used for grinding may typically be single or multistage roll mills, preferably two- or three-stage roll mills, pin mills, hammer mills or vibratory mills. Oversize gel lumps which often still have not dried on the inside are elastomeric, lead to problems in the grinding and are preferably removed before the grinding, which can be done in a simple manner by wind sifting or by means of a sieve ("guard sieve" for the mill). In view of the mill used, the mesh size of the sieve should be selected such that a minimum level of disruption resulting from oversize, elastomeric particles occurs.

Excessively large, insufficiently finely ground superabsorbent particles are perceptible as coarse particles in their predominant use, in hygiene products such as diapers; they also lower the mean initial swell rate of the superabsorbent. Both are undesired. Advantageously, coarse-grain polymer particles are therefore separated from the product. This is done by conventional classification processes, for example wind sifting, or by sieving through a sieve with a mesh size of at most 1000 μm, preferably at most 900 μm, more preferably at most 850 μm and most preferably at most 800

μm. For example, sieves of mesh size 700 μm, 650 μm or 600 μm are used. The coarse polymer particles ("oversize") removed may, for cost optimization, be sent back to the grinding and sieving cycle or be processed further separately.

Polymer particles with too small a particle size lower the permeability (SFC). Advantageously, this classification therefore also removes fine polymer particles. This can, if sieving is effected, conveniently effected through a sieve of mesh size at most 300 μm, preferably at most 200 μm, more preferably at most 150 μm and most preferably at most 100 μm. The fine polymer particles ("undersize" or "fines") removed can, for cost optimization, be sent back as desired to the monomer stream, to the polymerizing gel, or to the fully polymerized gel before the drying of the gel.

The mean particle size of the polymer particles removed as the product fraction is generally at least 200 μm, preferably at least 250 μm and more preferably at least 300 μm, and generally at most 600 μm and more preferably at most 500 μm. The proportion of particles with a particle size of at least 150 μm is generally at least 90% by weight, more preferably at least 95% by weight and most preferably at least 98% by weight. The proportion of particles with a particle size of at most 850 μm is generally at least 90% by weight, more preferably at least 95% by weight and most preferably at least 98% by weight.

In some other known production processes for superabsorbents, especially in the case of suspension polymerization, spray or dropletization polymerization, the selection of the process parameters defines the particle size distribution. These processes directly give rise to particulate superabsorbents of the desired particle size, such that grinding and sieving steps can often be dispensed with. In some processes (especially in the case of spray or dropletization polymerization), a dedicated drying step can often also be dispensed with.

The polymer thus prepared has superabsorbent properties and is covered by the term "superabsorbent". Its CRC is typically comparatively high, but its AUL or SFC comparatively low. A surface nonpostcrosslinked superabsorbent of this type is often referred to as "base polymer" to distinguish it from a surface postcrosslinked superabsorbent produced therefrom.

The base polymer is optionally surface postcrosslinked. Surface postcrosslinkers for superabsorbents and processes for surface postcrosslinking of superabsorbents are well-known. Suitable postcrosslinkers are compounds which comprise groups which can form bonds with at least two functional groups of the superabsorbent particles. In the case of the acrylic acid/sodium acrylate-based superabsorbents prevalent on the market, suitable surface postcrosslinkers are compounds which comprise groups which can form bonds with at least two carboxylate groups. Rather than "surface postcrosslinker" or "surface postcrosslinking", merely "postcrosslinker" or "postcrosslinking" are often also used.

Preferred surface postcrosslinkers are di- or triglycidyl compounds, for example glycidyl ethers, for instance ethylene glycol diglycidyl ether and glycerol di- or triglycidyl ether.

Preferred surface postcrosslinkers are also 2-oxazolidones such as 2-oxazolidone and N-(2-hydroxyethyl)-2-oxazolidone, N-methyl-2-oxazolidone, N-acyl-2-oxazolidones such as N-acetyl-2-oxazolidone, 2-oxotetrahydro-1,3-oxazine, bicyclic amide acetals such as 5-methyl-1-aza-4,6-dioxabicyclo[3.3.0]octane, 1-aza-4,6-dioxabicyclo[3.3.0]-octane and 5-isopropyl-1-aza-4,6-dioxabicyclo[3.3.0]octane, bis-2-oxazolidones and poly-2-oxazolidones. Among these, particular preference is given to 2-oxazolidone, N-methyl-2-oxazolidone, N-(2-hydroxyethyl)-2-oxazolidone and N-hydroxypropyl-2-oxazolidone.

Further preferred postcrosslinkers are propane-1,3-diol, pentane-1,5-diol, hexane-1,6-diol and heptane-1,7-diol, butane-1,3-diol, octane-1,8-diol, nonane-1,9-diol and decane-1,10-diol. Among these, particular preference is given to those that are water-soluble at 23° C. to an extent of at least 30% by weight, preferably to an extent of at least 40% by weight, more preferably to an extent of at least 50% by weight, most preferably at least to an extent of 60% by weight, for example propane-1,3-diol and heptane-1,7-diol. Even more preferred are those that are liquid at 25° C.

Further preferred postcrosslinkers are butane-1,2,3-triol, butane-1,2,4-triol, glycerol, trimethylolpropane, trimethylolethane, pentaerythritol, 1- to 3-tuply (per molecule) ethoxylated glycerol, trimethylolethane or trimethylolpropane and 1- to 3-tuply (per molecule) propoxylated glycerol, trimethylolethane or trimethylolpropane. Additionally preferred are 2-tuply ethoxylated or propoxylated neopentyl glycol. Particular preference is given to 2-tuply and 3-tuply ethoxylated glycerol, neopentyl glycol, 2-methylpropane-1,3-diol and trimethylolpropane. Among these, particular preference is given to those that have a viscosity at 23° C. of less than 3000 mPas, preferably less than 1500 mPas, more preferably less than 1000 mPas, especially preferably less than 500 mPas and very especially preferably less than 300 mPas.

Further preferred postcrosslinkers are ethylene carbonate and propylene carbonate.

A further preferred postcrosslinker is 2,2'-bis(2-oxazoline).

These preferred postcrosslinkers minimize side reactions and subsequent reactions which lead to volatile and hence malodorous compounds. The superabsorbents produced with the preferred postcrosslinkers are therefore odor-neutral even in the moistened state.

It is possible to use an individual postcrosslinker or any desired mixtures of different postcrosslinkers.

The postcrosslinker is generally used in an amount of at least 0.001% by weight, preferably of at least 0.02% by weight, more preferably of at least 0.05% by weight, and generally at most 2% by weight, preferably at most 1% by weight, more preferably at most 0.3% by weight, for example at most 0.15% by weight or at most 0.095% by weight, based in each case on the mass of the base polymer contacted therewith (for example the sieve fraction in question).

The postcrosslinking is typically performed in such a way that a solution of the postcrosslinker is sprayed onto the dried base polymer particles. After the spray application, the polymer particles coated with postcrosslinker are dried thermally, and the postcrosslinking reaction can take place either before or during the drying. If surface postcrosslinkers with polymerizable groups are used, the surface postcrosslinking can also be effected by means of free-radically induced polymerization of such groups by means of common free-radical formers or else by means of high-energy radiation, for example UV light. This can be done in parallel with or instead of the use of postcrosslinkers which form covalent or ionic bonds to functional groups at the surface of the base polymer particles.

The spray application of the postcrosslinker solution is preferably carried out in mixers with moving mixing tools, such as screw mixers, disk mixers, paddle mixers or shovel mixers, or mixers with other mixing tools. Particular preference is given, however, to vertical mixers. It is also possible to spray on the postcrosslinker solution in a fluidized bed. Suitable mixers are obtainable, for example, as Pflugschar® plowshare mixers from Gebr. Lödige Maschinenbau GmbH, Elsener-Strasse 7-9, 33102 Paderborn, Germany, or as Schugi® Flexomix® mixers, Vrieco-Nauta® mixers or Turbulizer® mixers from Hosokawa Micron BV, Gildenstraat 26, 7000 AB Doetinchem, the Netherlands.

The spray nozzles usable are not subject to any restriction. Suitable nozzles and atomization systems are described, for example, in the following references: Zerstäuben von Flüssigkeiten [Atomization of Liquids], Expert-Verlag, vol. 660, Reihe Kontakt & Studium, Thomas Richter (2004) and in Zerstäubungstechnik [Atomization Technology], Springer-Verlag, VDI-Reihe, Gunter Wozniak (2002). It is possible to use mono- and polydisperse spray systems. Among the polydisperse systems, one-phase pressurized nozzles (jet- or lamella-forming), rotary atomizers, two-phase atomizers, ultrasound atomizers and impingement nozzles are suitable. In the case of the two-phase atomizers, the liquid phase can be mixed with the gas phase either internally or externally. The spray profile of the nozzles is uncritical and may assume any desired form, for example a round jet, flat jet, wide angle round jet or circular ring spray profile. It is advantageous to use a nonoxidizing gas if two-phase atomizers are used, particular preference being given to nitrogen, argon or carbon dioxide. The liquid to be sprayed can be supplied to such nozzles under pressure. The atomization of the liquid to be sprayed can be effected by expanding it in the nozzle bore on attainment of a particular minimum velocity. In addition, it is also possible to use one-phase nozzles for the inventive purpose, for example slit nozzles or swirl chambers (full-cone nozzles) (for example from Dusen-Schlick GmbH, Germany, or from Spraying Systems Deutschland GmbH, Germany). Such nozzles are also described in EP 0 534 228 A1 and EP 1 191 051 A2.

The postcrosslinkers are typically used in the form of an aqueous solution. If exclusively water is used as the solvent, a surfactant or deagglomeration assistant is advantageously added to the postcrosslinker solution or actually to the base polymer. This improves the wetting characteristics and reduces the tendency to form lumps.

All anionic, cationic, nonionic and amphoteric surfactants are suitable as deagglomeration assistants, but preference is given to nonionic and amphoteric surfactants for skin compatibility reasons. The surfactant may also comprise nitrogen. For example, sorbitan monoesters, such as sorbitan monococoate and sorbitan monolaurate, or ethoxylated variants thereof, for example Polysorbat 20®, are added. Further suitable deagglomeration assistants are the ethoxylated and alkoxylated derivatives of 2-propylheptanol, which are sold under the Lutensol XL® and Lutensol XP® brands (BASF SE, Carl-Bosch-Strasse 38, 67056 Ludwigshafen, Germany).

The deagglomeration assistant can be metered in separately or added to the postcrosslinker solution. Preference is given to simply adding the deagglomeration assistant to the postcrosslinker solution.

The amount of the deagglomeration assistant used, based on base polymer, is, for example, 0% to 0.1% by weight, preferably 0% to 0.01% by weight, more preferably 0% to 0.002% by weight. The deagglomeration assistant is preferably metered in such that the surface tension of an aqueous extract of the swollen base polymer and/or of the swollen postcrosslinked water-absorbing polymer at 23° C. is at least 0.060 N/m, preferably at least 0.062 N/m, more preferably at least 0.065 N/m, and advantageously at most 0.072 N/m.

The aqueous postcrosslinker solution may, as well as the at least one postcrosslinker, also comprise a cosolvent. The content of nonaqueous solvent or total amount of solvent can be used to adjust the penetration depth of the postcrosslinker into the polymer particles. Industrially readily available cosolvents are C1-C6 alcohols such as methanol, ethanol, n-propanol, isopropanol, n-butanol, sec-butanol, tert-butanol or 2-methyl-1-propanol, $C_2$-$C_5$ diols such as ethylene glycol, 1,2-propylene glycol or butane-1,4-diol, ketones such as acetone, or carboxylic esters such as ethyl acetate. A disadvantage of some of these cosolvents is that they have typical intrinsic odors.

The cosolvent itself is ideally not a postcrosslinker under the reaction conditions. However, it may arise in the boundary case and depending on the residence time and temperature that the cosolvent contributes partly to crosslinking. This is the case especially when the postcrosslinker is relatively slow to react and can therefore also constitute its own cosolvent, as is the case, for example, when cyclic carbonates, diols or polyols are used. Such postcrosslinkers can also be used in the function as a cosolvent in a mixture with more reactive postcrosslinkers, since the actual postcrosslinking reaction can then be performed at lower temperatures and/or with shorter residence times than in the absence of the more reactive crosslinker. Since the cosolvent is used in relatively large amounts and some also remains in the product, it must not be toxic.

In the process of the invention, the abovementioned diols and polyols and also the cyclic carbonates are also suitable as cosolvents. They fulfill this function in the presence of a comparatively reactive postcrosslinker and/or of a di- or triglycidyl compound. Preferred cosolvents in the process of the invention are, however, especially the diols mentioned, especially when a reaction of the hydroxyl groups is sterically hindered by neighboring groups. Although such diols are also suitable in principle as postcrosslinkers, this requires significantly higher reaction temperatures or optionally higher use amounts than for sterically unhindered diols.

Particularly preferred combinations of low-reactivity postcrosslinker as a cosolvent and reactive postcrosslinker are combinations of the polyhydric alcohols, diols and polyols mentioned with the stated amide acetals or carbamates. Suitable combinations are, for example, 2-oxazolidone/propane-1,2-diol and N-(2-hydroxyethyl)-2-oxazolidone/propane-1,2-diol, and also ethylene glycol diglycidyl ether/propane-1,2-diol. Very particularly preferred combinations are 2-oxazolidone/propane-1,3-diol and N-(2-hydroxyethyl)-2-oxazolidone/propane-1,3-diol. Further preferred combinations are those with ethylene glycol diglycidyl ether or glyceryl di- or triglycidyl ether with the following solvents, cosolvents or cocrosslinkers: isopropanol, propane-1,3-diol, 1,2-propylene glycol or mixtures thereof. Further preferred combinations are those with 2-oxazolidone or (2-hydroxyethyl)-2-oxazolidone in the following solvents, cosolvents or cocrosslinkers: isopropanol, propane-1,3-diol, 1,2-propylene glycol, ethylene carbonate, propylene carbonate or mixtures thereof.

Frequently, the concentration of the cosolvent in the aqueous postcrosslinker solution is from 15 to 50% by weight, preferably from 15 to 40% by weight and more preferably from 20 to 35% by weight, based on the postcrosslinker solution. In the case of cosolvents which have only limited miscibility with water, the aqueous postcrosslinker solution will advantageously be adjusted such that only one phase is present, optionally by lowering the concentration of the cosolvent.

In a preferred embodiment, no cosolvent is used. The postcrosslinker is then employed only as a solution in water, optionally with addition of a deagglomeration assistant.

The concentration of the at least one postcrosslinker in the aqueous postcrosslinker solution is typically from 1 to 20% by weight, preferably from 1.5 to 10% by weight and more preferably from 2 to 5% by weight, based on the postcrosslinker solution.

The total amount of the postcrosslinker solution based on base polymer is typically from 0.3 to 15% by weight and preferably from 2 to 6% by weight.

The actual surface postcrosslinking by reaction of the surface postcrosslinker with functional groups at the surface of the base polymer particles is usually carried out by heating the base polymer wetted with surface postcrosslinker solution, typically referred to as "drying" (but not to be confused with the above-described drying of the polymer gel from the polymerization, in which typically very much more liquid has to be removed). The drying can be effected in the mixer itself, by heating the jacket, by means of heat exchange surfaces or by blowing in warm gases. Simultaneous admixing of the superabsorbent with surface postcrosslinker and drying can be effected, for example, in a fluidized bed drier. The drying is, however, usually carried out in a downstream drier, for example a tray drier, a rotary tube oven, a paddle or disk drier or a heatable screw. Suitable driers are obtainable, for example, as Solidair® or Torusdisc® driers from Bepex International LLC, 333 N.E. Taft Street, Minneapolis, Minn. 55413, U.S.A., or as paddle or shovel driers or else as fluidized bed driers from Nara Machinery Co., Ltd., European office, Europaallee 46, 50226 Frechen, Germany.

It is possible to heat the polymer particles by means of contact surfaces in a downstream drier for the purpose of drying and performing the surface postcrosslinking, or by means of warm inert gas supply, or by means of a mixture of one or more inert gases with steam, or only with steam alone. In the case of supply of the heat by means of contact surfaces, it is possible to perform the reaction under inert gas at slightly or completely reduced pressure. In the case of use of steam for direct heating of the polymer particles, it is desirable in accordance with the invention to operate the drier under standard pressure or elevated pressure. In this case, it may be advisable to split up the postcrosslinking step into a heating step with steam and a reaction step under inert gas but without steam. This can be achieved in one or more apparatuses. According to the invention, the polymer particles can be heated with steam as early as in the postcrosslinking mixer. The base polymer used may still have a temperature of from 10 to 120° C. from preceding process steps; the postcrosslinker solution may have a temperature of from 0 to 70° C. In particular, the postcrosslinker solution can be heated to reduce the viscosity.

Preferred drying temperatures are in the range of 100 to 250° C., preferably 120 to 220° C., more preferably 130 to 210° C. and most preferably 150 to 200° C. The preferred residence time at this temperature in the reaction mixer or dryer is preferably at least 10 minutes, more preferably at least 20 minutes, most preferably at least 30 minutes, and typically at most 60 minutes. Typically, the drying is conducted such that the superabsorbent has a residual moisture content of generally at least 0.1% by weight, preferably at least 0.2% by weight and most preferably at least 0.5% by weight, and generally at most 15% by weight, preferably at most 10% by weight and more preferably at most 8% by weight.

The postcrosslinking can take place under standard atmospheric conditions. "Standard atmospheric conditions" means that no technical precautions are taken in order to reduce the partial pressure of oxidizing gases, such as that of the atmospheric oxygen, in the apparatus in which the postcrosslinking reaction predominantly takes place (the "postcrosslinking reactor", typically the drier). However, preference is given to performing the postcrosslinking reaction under reduced partial pressure of oxidizing gases. Oxidizing gases are substances which, at 23° C., have a vapor pressure of at least 1013 mbar and act as oxidizing agents in combustion processes, for example oxygen, nitrogen oxide and nitrogen dioxide, especially oxygen. The partial pressure of oxidizing gases is preferably less than 140 mbar, preferably less than 100 mbar, more preferably less than 50 mbar and most preferably less than 10 mbar. When the thermal postcrosslinking is carried out at ambient pressure, i.e. at a total pressure around 1013 mbar, the total partial pressure of the oxidizing gases is determined by their proportion by volume. The proportion of the oxidizing gases is preferably less than 14% by volume, preferably less than 10% by volume, more preferably less than 5% by volume and most preferably less than 1% by volume.

The postcrosslinking can be carried out under reduced pressure, i.e. at a total pressure of less than 1013 mbar. The total pressure is typically less than 670 mbar, preferably less than 480 mbar, more preferably less than 300 mbar and most preferably less than 200 mbar. When drying and postcrosslinking are carried out under air with an oxygen content of 20.8% by volume, the partial oxygen pressures corresponding to the abovementioned total pressures are 139 mbar (670 mbar), 100 mbar (480 mbar), 62 mbar (300 mbar) and 42 mbar (200 mbar), the respective total pressures being in the brackets. Another means of lowering the partial pressure of oxidizing gases is the introduction of nonoxidizing gases, especially inert gases, into the apparatus used for postcrosslinking. Suitable inert gases are substances that are in gaseous form in the postcrosslinking drier at the postcrosslinking temperature and the given pressure and do not have an oxidizing action on the constituents of the drying polymer particles under these conditions, for example nitrogen, carbon dioxide, argon, steam, preference being given to nitrogen. The amount of inert gas is generally from 0.0001 to 10 $m^3$, preferably from 0.001 to 5 $m^3$, more preferably from 0.005 to 1 $m^3$ and most preferably from 0.005 to 0.1 $m^3$, based on 1 kg of superabsorbent.

In the process of the invention, the inert gas, if it does not comprise steam, can be blown into the postcrosslinking drier via nozzles; however, particular preference is given to adding the inert gas to the polymer particle stream via nozzles actually within or just upstream of the mixer, by admixing the superabsorbent with surface postcrosslinker.

It will be appreciated that vapors of cosolvents removed from the drier can be condensed again outside the drier and optionally recycled.

Before, during or after the postcrosslinking, in addition to the organic postcrosslinkers mentioned that form covalent bonds with carboxyl groups in the superabsorbent, aluminum ions are applied to the surfaces of the superabsorbent of the invention, or, if no surface postcrosslinking with one of the organic postcrosslinkers mentioned is conducted, in lieu thereof. As already stated above, this application of aluminum ions is in principle an (optionally additional) surface postcrosslinking by ionic, noncovalent bonds and is referred to in the context of this invention, for distinction from surface postcrosslinking by means of covalent bonds, as "complexation" with the metal ions in question.

This application of aluminum ions is effected by adding an aqueous solution comprising aluminum ions, which has the feature that it comprises aluminum ions in a proportion within the range of 0.5%-15% by weight (converted if appropriate to A3+), based on the total mass of the solution, and further comprises anions of lactic acid (lactate ions) and phosphoric acid (phosphate ions), where the molar proportion of the lactate ions is within the range of 0.01-2.99 times the molar amount of $Al^{3+}$ and the molar proportion of the phosphate ions is within the range of 0.01-2.99 times the molar amount of $Al^{3+}$.

The addition is preferably effected in such a way that the surfaces of the superabsorbent particles of the base polymer or of the already surface postcrosslinked polymer are wetted homogeneously with the solution. In principle, this is effected in the same way as described for the organic surface postcrosslinker, including the drying step. The spray application of the aluminum solution to the superabsorbent particles may either precede or follow the surface postcrosslinking. In a particularly preferred process, the spray application of the aluminum solution is effected in the same step together with the spray application of the crosslinker solution, in which case the two solutions are sprayed on separately in succession or simultaneously via two nozzles, or crosslinker solution and metal salt solution can be sprayed on jointly via one nozzle.

If a drying step is carried out after the surface postcrosslinking and/or treatment with complexing agent, it is advantageous but not absolutely necessary to cool the product after the drying. The cooling can be effected continuously or batchwise; to this end, the product is conveniently conveyed continuously into a cooler arranged downstream of the drier. Any apparatus known for removal of heat from pulverulent solids can be used for this purpose, more particularly any device mentioned above as drying apparatus, except that it is charged not with a heating medium but with a cooling medium, for example with cooling water, such that no heat is introduced into the superabsorbent via the walls and, according to the construction, also via the stirring elements or other heat exchange surfaces, and is instead removed therefrom. Preference is given to the use of coolers in which the product is moved, i.e. cooled mixers, for example shovel coolers, disk coolers or paddle coolers. The superabsorbent can also be cooled in a fluidized bed by injecting a cooled gas such as cold air. The cooling conditions are adjusted so as to obtain a superabsorbent with the temperature desired for further processing. Typically, a mean residence time in the cooler of generally at least 1 minute, preferably at least 3 minutes and more preferably at least 5 minutes, and generally at most 6 hours, preferably at most 2 hours and more preferably at most 1 hour is established, and the cooling performance is such that the product obtained has a temperature of generally at least 0° C. preferably at least 10° C. and more preferably at least 20° C., and generally at most 100° C., preferably at most 80° C. and more preferably at most 60° C.

The surface postcrosslinked superabsorbent is optionally ground and/or sieved in a customary manner. Grinding is typically not required here, but the removal by sieving of agglomerates or fines formed is usually appropriate for establishment of the desired particle size distribution of the product. Agglomerates and fines are either discarded or preferably recycled into the process in a known manner at a suitable point, agglomerates after comminution. The particle sizes desired for surface postcrosslinked superabsorbents are the same as for base polymers.

Optionally, the superabsorbents of the invention that have been produced by the process of the invention are provided with further additions, nonlimiting examples being those that provide stabilization against discoloration, reduce the tendency to caking or further increase the permeability. For this purpose, all known additives can be used in the manner known for each in the process of the invention. Examples of known additions that provide stabilization against discoloration are the abovementioned sulfonic acid or phosphonic acid derivatives, which can also be applied after the production of the superabsorbent of the invention rather than or as well as the addition during the production thereof. Examples of known additions that reduce the caking tendency of the superabsorbent or further increase the permeability are water-insoluble inorganic powders.

Preference is given to adding a water-insoluble inorganic powder to the superabsorbent of the invention. Preference is given to using precipitated silicon dioxide or silicon dioxide produced by pyrolysis, or else aluminum oxide produced by pyrolysis. Pyrogenic silicon dioxide is available, for example, under the AEROSIL® brand, and pyrogenic aluminum oxide, for example, under the AEROXIDE® Alu brand from Evonik Industries AG, Inorganic Materials, Rodenbacher Chaussee 4, 63457 Hanau-Wolfgang, Germany. Silicon dioxide produced by precipitation is available, for example, under the SIPERNAT® brand from Evonik Industries AG, Inorganic Materials, Rodenbacher Chaussee 4, 63457 Hanau-Wolfgang, Germany. The water-insoluble inorganic powders can also be hydrophobized by suitable surface treatment and are often supplied by manufacturers both in hydrophobized and in hydrophilic form. In the context of this invention, the use of hydrophilic water-insoluble inorganic powders is preferred.

In general, the water-insoluble inorganic powder is added to the superabsorbent in an amount of at least 0.005% by weight, preferably of at least 0.03% by weight and more preferably of at least 0.05% by weight, and generally of at most 6.0% by weight, preferably at most 1.0% by weight and more preferably at most 0.5% by weight, based in each case on the total weight of the anhydrous superabsorbent comprising inorganic powder.

Superabsorbents can be mixed with the optional additives by any known mixing process. When in solid form, they are incorporated by mixing in substance or as a suspension in a solvent or suspension medium, and, when in dissolved or liquid form, optionally also in solution or liquid form. Due to easier homogeneous distribution, the additives are preferably incorporated into the superabsorbent by mixing as a powder or suspension. This does not necessarily produce a physical mixture separable in a simple manner by mechanical measures. The additives may quite possibly enter into a more definite bond with the superabsorbent, for example in the form of a comparatively firmly adhering surface layer or in the form of particles adhering firmly to the surface of the superabsorbent particles. The mixing of the additives into the known superabsorbent can quite possibly also be understood and referred to as "coating".

If a solution or suspension is used for coating, the solvent or suspension medium used is a solvent or suspension medium which is chemically compatible both with the superabsorbent and with the additive, i.e. does not enter into any undesired chemical reactions therewith. Typically, water or an organic solvent is used, for example an alcohol or polyol, or mixtures thereof. Examples of suitable solvents or suspension media are water, isopropanol/water, propane-1, 3-diol/water and propylene glycol/water, where the mixing ratio by mass is preferably from 20:80 to 40:60. If a suspension medium is used for the stabilizers to be used in accordance with the invention or the inorganic particulate solid, water is preferred. A surfactant can be added to the solution or suspension.

Optional additives are, if they are not added to the monomer mixture or the polymerizing gel, generally mixed with the superabsorbent in exactly the same way as the solution or suspension which comprises a surface postcrosslinker and is applied to the superabsorbent for surface postcrosslinking. The additive can be applied as a constituent of the solution applied for surface postcrosslinking or of one of the components thereof to an (as yet) nonpostcrosslinked superabsorbent (a "base polymer"), i.e. the additive is added to the solution of the surface postcrosslinker or to one of the components thereof. The superabsorbent coated with surface postcrosslinker and additives then passes through the further process steps required for surface postcrosslinking, for example a thermally induced reaction of the surface postcrosslinker with the superabsorbent. This process is comparatively simple and economically viable.

If the superabsorbent is subjected to a cooling step after the surface postcrosslinking or the complexation, the optional additions can conveniently be mixed in in the cooler. If additives are applied as a solution or suspension, they can also be applied to the already surface postcrosslinked superabsorbent in the same mixing apparatuses as described for the application of the surface postcrosslinker to the base polymer. Usually, but not necessarily, this is followed by heating, just like in the surface postcrosslinking step, in order to dry the superabsorbent again. The temperature established in this drying operation is then, however, generally at most 110° C., preferably at most 100° C. and more preferably at most 90° C., in order to prevent undesired reactions of the additive. The temperature is adjusted such that, in view of the residence time in the drying unit, the desired water content of the superabsorbent is achieved. It is also entirely possible and convenient to add additives individually or together with other customary assistants, for example dust binders, anticaking agents or water for remoisturization of the superabsorbent. The temperature of the polymer particles in this case is between 0° C. and 190° C., preferably less than 160° C., more preferably less than 130° C., even more preferably less than 100° C. and most preferably less than 70° C. The polymer particles are optionally cooled rapidly after coating to temperatures below any decomposition temperature of the additive.

It is optionally possible to additionally apply to the surface of the superabsorbent particles, whether unpostcrosslinked or postcrosslinked, in any process step of the preparation process, if required, all known coatings, such as film-forming polymers, thermoplastic polymers, dendrimers, polycationic polymers (for example polyvinylamine, polyethyleneimine or polyallylamine), or all water-soluble mono- or polyvalent metal salts known to those skilled in the art, for example aluminum sulfate, sodium salts, potassium salts, zirconium salts or iron salts. Examples of useful alkali metal salts are sodium and potassium sulfate, and sodium and potassium lactates, citrates and sorbates. This allows additional effects, for example a reduced caking tendency of the end product or of the intermediate in the particular process step of the production process, improved processing properties or a further enhanced permeability (SFC), to be achieved. When additives are used and sprayed on in the form of dispersions, they are preferably used in the form of aqueous dispersions, and preference is given to additionally applying an antidusting agent to fix the additive on the surface of the superabsorbent. The antidusting agent is then either added directly to the dispersion of the inorganic pulverulent additive; optionally, it can also be added as a separate solution before, during or after the application of the inorganic pulverulent additive by spray application. Most preferred is the simultaneous spray application of postcrosslinking agent, antidusting agent and pulverulent inorganic additive in the postcrosslinking step. In a further preferred process variant, the antidusting agent is, however, added separately in the cooler, for example by spray application from above, below or from the side. Particularly suitable antidusting agents which can also serve to fix pulverulent inorganic additives on the surface of the water-absorbing polymer particles are polyethylene glycols with a molecular weight of 400 to 20 000 g/mol, polyglycerol, 3- to 100-tuply ethoxylated polyols, such as trimethylolpropane, glycerol, sorbitol and neopentyl glycol. Particularly suitable are 7- to 20-tuply ethoxylated glycerol or trimethylolpropane, for example Polyol TP 70® (Perstorp, Sweden). The latter have the advantage, more particularly, that they lower the surface tension of an aqueous extract of the water-absorbing polymer particles only insignificantly.

It is likewise possible to adjust the superabsorbent of the invention to a desired water content by adding water. It may also be advantageous to slightly swell the superabsorbent by addition of water and then adjust it back to the desired water content by drying.

All coatings, solids, additives and assistants can each be added in separate process steps, but the most convenient method is usually to add them—if they are not added during the admixing of the base polymer with surface postcrosslinking agent—to the superabsorbent in the cooler, for instance by spray application of a solution or addition in fine solid form or in liquid form.

The superabsorbents of the invention generally have a centrifuge retention capacity (CRC, for test method see below) of at least 5 g/g, preferably of at least 10 g/g and more preferably of at least 20 g/g. Typically, it is not more than 40 g/g for surface postcrosslinked superabsorbents, but it is often higher for base polymers.

The superabsorbents of the invention, if they have been surface postcrosslinked, typically have an absorption under load (AUL0.7 psi, for test method see below) of at least 10 g/g, preferably at least 14 g/g, more preferably at least 18 g/g and most preferably at least 22 g/g, and typically not more than 30 g/g.

The present invention further provides hygiene articles comprising superabsorbent of the invention, preferably ultrathin diapers, comprising an absorbent layer consisting of 50 to 100% by weight, preferably 60 to 100% by weight, more preferably 70 to 100% by weight, especially preferably 80 to 100% by weight and very especially preferably 90 to 100% by weight of superabsorbent of the invention, of course not including the envelope of the absorbent layer.

Very particularly advantageously, the superabsorbents of the invention are also suitable for production of laminates and composite structures, as described, for example, in US 2003/0181115 and US 2004/0019342. In addition to the hotmelt adhesives described in both documents for production of such novel absorbent structures, and especially the fibers, described in US 2003/0181115, composed of hotmelt adhesives to which the superabsorbent particles are bound, the superabsorbents of the invention are also suitable for production of entirely analogous structures using UV-crosslinkable hotmelt adhesives, which are sold, for example, as AC-Resin® (BASF SE, Ludwigshafen, Germany). These UV-crosslinkable hotmelt adhesives have the advantage of already being processible at 120 to 140° C.; they therefore have better compatibility with many thermoplastic substrates. A further significant advantage is that UV-crosslinkable hotmelt adhesives are very benign in toxicological terms and also do not cause any vaporization in the hygiene articles. A very significant advantage in connection with the superabsorbents of the invention is the property of the UV-crosslinkable hotmelt adhesives of lacking any tendency to yellow during processing and crosslinking. This is especially advantageous when ultrathin or partly transparent hygiene articles are to be produced. The combination of the superabsorbents of the invention with UV-crosslinkable hotmelt adhesives is therefore particularly advantageous. Suitable UV-crosslinkable hotmelt adhesives are described, for example, in EP 0 377 199 A2, EP 0 445 641 A1, U.S. Pat. No. 5,026,806, EP 0 655 465 A1 and EP 0 377 191 A2.

The superabsorbent of the invention can also be used in other fields of industry in which fluids, especially water or aqueous solutions, are absorbed. These fields are, for example, storage, packaging, transport (as constituents of packaging material for water- or moisture-sensitive articles, for instance for flower transport, and also as protection against mechanical effects); animal hygiene (in cat litter); food packaging (transport of fish, fresh meat; absorption of water, blood in fresh fish or meat packaging); medicine (wound plasters, water-absorbing material for burn dressings or for other weeping wounds), cosmetics (carrier material for pharmaceutical chemicals and medicaments, rheumatic plasters, ultrasonic gel, cooling gel, cosmetic thickeners, sunscreen); thickeners for oil/water or water/oil emulsions; textiles (moisture regulation in textiles, shoe insoles, for evaporative cooling, for instance in protective clothing, gloves, headbands); chemical engineering applications (as a catalyst for organic reactions, for immobilization of large functional molecules such as enzymes, as an adhesive in agglomerations, heat stores, filtration aids, hydrophilic components in polymer laminates, dispersants, liquefiers); as assistants in powder injection molding, in the building and construction industry (installation, in loam-based renders, as a vibration-inhibiting medium, assistants in tunnel excavations in water-rich ground, cable sheathing); water treatment, waste treatment, water removal (deicers, reusable sand bags); cleaning; agrochemical industry (irrigation, retention of melt water and dew deposits, composting additive, protection of forests from fungal/insect infestation, retarded release of active ingredients to plants); for firefighting or for fire protection; coextrusion agents in thermoplastic polymers (for example for hydrophilization of multilayer films); production of films and thermoplastic moldings which can absorb water (e.g. films which store rain and dew for agriculture; films comprising superabsorbents for maintaining freshness of fruit and vegetables which are packaged in moist films; superabsorbent-polystyrene coextrudates, for example for packaging foods such as meat, fish, poultry, fruit and vegetables); or as a carrier substance in active ingredient formulations (pharmaceuticals, crop protection).

The articles of the invention for absorption of fluid differ from known examples in that they comprise the superabsorbent of the invention.

A process for producing articles for absorption of fluid, especially hygiene articles, has also been found, said process comprising using at least one superabsorbent of the invention in the production of the article in question. In addition, processes for producing such articles using superabsorbents are known.

Test Methods

The superabsorbent is tested by the test methods described below.

The standard test methods described hereinafter and designated "NWSP" are described in: "Nonwovens Standards Procedures", 2015 edition, published jointly by EDANA (European Disposables and Nonwovens Association, Avenue Herrmann Debroux 46, 1160 Brussels, Belgium, www.edana.org) and INDA (Association of the Nonwoven Fabrics Industry, 1100 Crescent Green, Suite 115, Cary, N.C. 27518, U.S.A., www.inda.org). This publication is obtainable both from EDANA and from INDA.

All measurements described below should, unless stated otherwise, be conducted at an ambient temperature of 23±2° C. and a relative air humidity of 50±10%. The superabsorbent particles are mixed thoroughly before the measurement unless stated otherwise.

Centrifuge Retention Capacity (CRC)

The centrifuge retention capacity of the superabsorbent is determined to standard test method No. NWSP 241.0 R$^2$ (15) "Gravimetric Determination of the Fluid Retention Capacity in Saline Solution after Centrifugation".

Absorbency under a load of 0.7 psi (AUL0.7 psi)

The absorbency under a load of 4826 Pa (0.7 psi) of the superabsorbent is determined by the standard test method No. NWSP 242.0 R2 (15) "Gravimetric Determination of Absorption Against Pressure".

Moisture content of the superabsorbent (residual moisture, water content)

The water content of the superabsorbent particles is determined by standard test method No. NWSP 230.0 R2 (15) "Estimation of the Moisture Content as Weight Loss Upon Heating".

Permeability (SFC, "Saline Flow Conductivity")

The permeability of a swollen gel layer formed by the superabsorbent as a result of liquid absorption is determined under a pressure of 0.3 psi (2068 Pa), as described in EP 0 640 330 A1, as the gel layer permeability of a swollen gel layer of superabsorbent particles, the apparatus described in the aforementioned patent application on page 19 and in FIG. 8 being modified to the effect that the glass frit (40) is not used, and the plunger (39) consists of the same polymer material as the cylinder (37) and now comprises 21 bores of equal size distributed homogeneously over the entire contact area. The procedure and evaluation of the measurement remain unchanged from EP 0 640 330 A1. The flow is detected automatically.

The permeability (SFC) is calculated as follows:

$$SFC[cm^3 s/g] = (Fg(t=0) \times L0)/(d \times A \times WP)$$

where $Fg(t=0)$ is the flow of NaCl solution in g/s, which is obtained using linear regression analysis of the $Fg(t)$ data of the flow determinations by extrapolation to t=0, L0 is the thickness of the gel layer in cm, d is the density of the NaCl solution in g/cm$^3$, A is the area of the gel layer in cm$^2$, and WP is the hydrostatic pressure over the gel layer in dyn/cm$^2$.

Permeability (GBP, "Gel Bed Permeability")

The gel bed permeability is measured by the method in published patent application No. US 2005/0 256 757 A1, paragraphs [0061] to [0075].

CIE color number (L, a, b)

The color analysis is carried out according to the CIELAB method (Hunterlab, volume 8, 1996, book 7, pages 1 to 4) with a "LabScan XE S/N LX17309" colorimeter (Hunter-Lab, Reston, U.S.A.). This method describes the colors via the coordinates L, a and b of a three-dimensional system. L indicates the brightness, where L=0 means black and L=100 white. The values of a and b indicate the positions of the color on the red/green and yellow/blue color axes respectively, where +a represents red, −a represents green, +b represents yellow and −b represents blue.

The color measurement corresponds to the three-area method according to DIN 5033-6.

Aging Test

Measurement 1 (initial color): A plastic dish of internal diameter 9 cm is overfilled with superabsorbent particles which are then smoothed flat with a blade across the edge, and the CIE color numbers are determined.

Measurement 2 (after aging): A plastic dish of internal diameter 9 cm is filled with superabsorbent particles which are then smoothed flat with a blade across the edge.

The dish is then placed open into a climate-controlled cabinet heated to 70° C. with constant relative air humidity of 80%. After 7 days have passed, the dish is taken out. After cooling to room temperature, the CIE color numbers are determined. Subsequently, the dish is placed back into the climate-controlled cabinet and heated for a further 7 days. Subsequently, again after cooling to room temperature, the CIE color numbers are determined.

EXAMPLES

Bruggolite® FF6 is a mixture of the disodium salt of 2-hydroxy-2-sulfinatoacetic acid, the disodium salt of 2-hydroxy-2-sulfonatoacetic acid and sodium bisulfite, available from L. Bruggemann KG, Salzstrasse 131, 74076 Heilbronn, Germany Laromer® LR 9015X is the triacrylate of fifteen-tuply ethoxylated trimethylolpropane, available from BASF SE, Ludwigshafen, Germany. DAROCUR® 1173 is 2-hydroxy-2-methyl-1-phenylpropan-1-one, available from BASF Schweiz AG, Basle, Switzerland. IRGACURE® 651 is 2,2-dimethoxy-1,2-diphenylethan-1-one, likewise available from BASF Schweiz AG, Basle, Switzerland.

Lohtragon® ALA 200 is 20% by weight aqueous solution of aluminum dihydroxymonoacetate, available from Dr. Paul Lohmann GmbH KG, 31857 Emmerthal, Germany. Lohtragon® ACE is an aqueous solution, obtainable from the same source, of aluminum dihydroxymonoacetate having an aluminum content of 4.2% by weight. The aluminum salt solutions identified here by their batch numbers can likewise be purchased from that source.

The mixer used in the examples for surface postcrosslinking and complexation was a Pflugschar® M5 plowshare mixer with a heating jacket from Gebr. Lödige Maschinenbau GmbH; Elsener Strasse 7-9, 33102 Paderborn, Germany. To measure the temperature of the product in the mixer, a thermocouple was introduced into the opening provided for the purpose in the mixer to such an extent that its tip was at a distance from the heated inner wall of the mixer and was within the product, but could not be impacted by the mixing tools.

In the examples, the aluminum salt solutions in table 1 below were used. These were produced by initially charging the water in a reaction vessel, adding aluminum hydroxide hydrate while stirring, adding lactic acid, phosphoric acid and acids of the other anions mentioned in each case, and stirring the resulting mixture. The salt solutions mentioned are also obtainable from Dr. Paul Lohmann GmbH KG, Hauptstrasse 2, 31860 Emmerthal, Germany.

TABLE 1

(all amounts stated in % by weight based on the solution)

| Batch No. | Al | Lactate | $PO_4^{3-}$ | Others | $OH^-$ | $H_2O$ |
|---|---|---|---|---|---|---|
| 1085250 | 3.3 | 5.5 | 5.9 | maleate, 8.1 | 3.0 | 74.2 |
| 1085251 | 2.7 | 8.9 | 4.8 | — | 2.3 | 80.1 |
| 1085252 | 3.7 | 10.2 | 6.5 | citrate, 1.4 | 3.1 | 75.1 |
| 1086562 | 3.4 | 9.8 | 1.8 | sulfate, 5.3 | 7.3 | 72.4 |
| 1086563 | 3.3 | 4.9 | 7.0 | sulfate, 5.3 | 5.9 | 73.6 |
| 1099550 | 3.0 | 13.2 | 9.9 | — | 1.6 | 72.3 |
| 1099551 | 4.1 | — | 16.7 | sulfate, 12.7 | 2.5 | 64.0 |
| 1099552 | 3.0 | — | 11.4 | sulfate, 17.3 | 1.6 | 66.7 |

Example 1

1 kg of superabsorbent base polymer (HySorb® T 9600 base polymer, surface nonpostcrosslinked crosslinked polymer of acrylic acid and sodium acrylate with neutralization level 72 mol %, available from BASF SE, Ludwigshafen, Germany) was initially charged in a mixer. At 40° C. and a shaft speed of 200 revolutions per minute, by means of a two-phase spray nozzle, a solution of 10 g of propane-1,2-diol, 1 g of a mixture of equal parts by weight of 2-hydroxyethyloxazolidinone (HEONON) and propane-1,3-diol, and 40 g of the aluminum salt solution batch #1085250 were sprayed on. Subsequently, the shaft speed was reduced to 70 revolutions per minute, and the product temperature was increased to 180° C. within 5 to 10 minutes and then maintained for 80 minutes.

Over this period, after 20, 30, 40, 50, 60 and 70 minutes, the mixer was stopped briefly and a sample of about 10 g of product was taken each time. All samples and the remaining amount of the product after 80 minutes were left to cool down to room temperature. The finished product was obtained by sieving to the particle size range from 150 μm to 710 μm. The measurements reported in table 2 were measured on the samples and on the finished product thus obtained by sieving.

Example 2

Example 1 was repeated, except that the solution of batch #1085250 was replaced with solution of batch #1085251. The measurements obtained are reported in table 2.

Example 3

Example 1 was repeated, except that the solution of batch #1085250 was replaced with solution of batch #1085252. The measurements obtained are reported in table 2.

Example 4

Example 1 was repeated, except that the solution of batch #1085250 was replaced with solution of batch #1085262. The measurements obtained are reported in table 2.

Example 5

Example 1 was repeated, except that the solution of batch #1085250 was replaced with solution of batch #1085263. The measurements obtained are reported in table 2.

Evaluation

Examples 1 to 5 show how the gel stiffness rises over the reaction time of the complexation, recognizable by the AUL value. Good to excellent GBP values are achieved with only slightly impaired CRC values.

Example 6

1 kg of superabsorbent base polymer (HySorb® T 9600 base polymer, surface nonpostcrosslinked crosslinked polymer of acrylic acid and sodium acrylate with neutralization level 72 mol %, available from BASF SE, Ludwigshafen, Germany) was initially charged in a mixer. At 40° C. and a shaft speed of 200 revolutions per minute, by means of a two-phase spray nozzle, a solution of 10 g of propane-1,2-diol, 1 g of a mixture of equal parts by weight of 2-hydroxyethyloxazolidinone (HEONON) and propane-1,3-diol, and 26.7 g of the aluminum salt solution batch #1099550 were sprayed on. Subsequently, the shaft speed was reduced to 70 revolutions per minute, and the product temperature was increased to 190° C. within 5 to 10 minutes and then maintained for 80 minutes. Over this period, after 20, 30, 40, 50, 60 and 70 minutes, the mixer was stopped briefly and a sample of about 10 g of product was taken each time. All samples and the remaining amount of the product after 80 minutes were left to cool down to room temperature. Thereafter, the product was left to cool down to room temperature. The finished product was obtained by sieving to the particle size range from 150 μm to 710 μm. The measurements reported in table 3 were measured on the samples and on the product thus obtained by sieving.

Example 6a

Example 6 was repeated, but kept at 190° C. for only 45 min and without taking of samples. The measurements are reported in table 4.

TABLE 2

(in all tables "—" means not determined)

| | 1 | | | 2 | | | 3 | | | 4 | | | 5 | | |
|---|---|---|---|---|---|---|---|---|---|---|---|---|---|---|---|
| Ex. Time [min] | CRC [g/g] | AUL 0.7 psi [g/g] | GBP [Da] | CRC [g/g] | AUL 0.7 psi [g/g] | GBP [Da] | CRC [g/g] | AUL 0.7 psi [g/g] | GBP [Da] | CRC [g/g] | AUL 0.7 psi [g/g] | GBP [Da] | CRC [g/g] | AUL 0.7 psi [g/g] | GBP [Da] |
| 20 | 40.9 | 8.4 | — | 33.2 | 22.4 | — | 33.3 | 21.0 | — | 31.2 | 21.9 | — | 31.2 | 21.7 | — |
| 30 | 38.8 | 13.7 | — | 31.5 | 22.1 | — | 30.2 | 21.4 | — | 29.4 | 21.8 | — | 29.8 | 22.0 | — |
| 40 | 35.9 | 19.1 | — | 31.1 | 21.7 | — | 31.0 | 20.9 | — | 28.9 | 21.5 | — | 30.7 | 21.7 | — |
| 50 | 35.1 | 21.7 | — | 29.7 | 21.5 | — | 30.2 | 21 | — | 29.2 | 20.9 | — | 28.7 | 21.1 | — |
| 60 | 36.1 | 22.7 | — | 28.4 | 21.2 | — | 28.8 | 20.6 | — | 26.5 | 20.6 | — | 26.8 | 20.4 | — |
| 70 | 34.9 | 22.9 | — | 26.5 | 20.8 | — | 27.5 | 20.4 | — | 26.8 | 20.3 | — | 28.3 | 20.3 | — |
| 80 | 33.2 | 23.2 | 29.4 | 27.8 | 20.4 | 77.6 | 28.4 | 20.4 | 64.6 | 28.8 | 20.2 | 76.8 | 27.0 | 20.4 | 52.2 |

TABLE 3

| | 6 | | | 7 | | | 8 | | |
|---|---|---|---|---|---|---|---|---|---|
| Ex. Time [min] | CRC [g/g] | AUL 0.7 psi [g/g] | GBP [Da] | CRC [g/g] | AUL 0.7 psi [g/g] | GBP [Da] | CRC [g/g] | AUL 0.7 psi [g/g] | GBP [Da] |
| 20 | 39.5 | 9.3 | — | 41.1 | 8.4 | — | 41.6 | 7.3 | — |
| 30 | 36.2 | 15.8 | — | 37.1 | 17.5 | — | 39.2 | 10.7 | — |
| 40 | 34.2 | 18.4 | — | 34.6 | 20.5 | — | 37.7 | 15.8 | — |
| 50 | 34.2 | 19.2 | 52.4 | 33.1 | 20.8 | 3.9 | 36.6 | 19.0 | — |
| 60 | 32.6 | 19.2 | — | 35.4 | 20.5 | — | 36.0 | 20.9 | — |
| 70 | 32.2 | 18.9 | — | 31.7 | 20.3 | — | 34.6 | 20.9 | — |
| 80 | 31.0 | 19.4 | 60.3 | 30.9 | 20.0 | 8.0 | 34.0 | 21.0 | 7.3 |

TABLE 4

| Example | Time [min] | CRC [g/g] | AUL 0.7 psi [g/g] | GBP [Da] | Initial color | | | Color after 7 days | | | Color after 14 days | | |
|---|---|---|---|---|---|---|---|---|---|---|---|---|---|
| | | | | | L | a | b | L | a | b | L | a | b |
| 6a | 45 | 34.4 | 18.7 | 44.2 | 93.7 | −0.8 | 4.9 | 68.5 | 6.3 | 17.4 | 45 | 11 | 19 |
| 7a | 45 | 35.0 | 20.6 | 3.6 | 90.9 | −0.6 | 4.1 | 59.4 | 8.2 | 20.6 | 31 | 11 | 13 |
| 8 | 80 | 34.0 | 21.0 | 7.3 | 93.1 | −0.6 | 4.4 | 60.7 | 7.9 | 19.9 | 33 | 11 | 14 |

Example 7 (Comparative)

Example 6 was repeated, except that the 26.7 g of solution of batch #1099550 were replaced with 19.5 g of solution of batch #1099551. The measurements obtained are reported in table 3.

Example 7a (Comparative)

Example 7 was repeated, but kept at 190° C. for only 45 min and without taking of samples. The measurements are reported in table 4.

Example 8 (Comparative)

Example 6 was repeated, except that the solution of batch #1099550 was replaced by solution of batch #1099552 and the temperature after application of the surface postcrosslinking solution was increased to 180° C. rather than 190° C.

The measurements show that neither in the case of the equivalent replacement of lactate with sulfate (3 mol of sulfate rather than 6 mol of lactate, i.e. replacement taking account of valency) in examples 7 and 7a nor in the case of equimolar replacement (1 mol of sulfate rather than 1 mol of lactate) in example 8 is the permeability or the color stability of the superabsorbents of the invention attained. This shows that solubility of aluminum phosphate can be achieved via addition of sulfate, but the use of this combination of salts in superabsorbents brings disadvantages compared to the superabsorbents of the invention.

The invention claimed is:

1. A superabsorbent complexed with aluminum ions, where the aluminum ions are applied in the form of an aqueous solution comprising aluminum ions in a proportion within a range of 0.5%-15% by weight (converted to $Al^{3+}$), based on a total mass of the solution, and further comprises anions of lactic acid (lactate ions) and phosphoric acid (phosphate ions), where a molar proportion of the lactate ions is within the range of 0.01-2.99 times a molar amount of $Al^{3+}$ and a molar proportion of the phosphate ions is within the range of 0.01-2.99 times the molar amount of $Al^{3+}$.

2. The superabsorbent according to claim 1, wherein the aluminum ions are applied in the form of an aqueous solution further comprising an anion of at least one third acid, where the third acid is selected from the group consisting of amino acids, carboxylic acids, citric acid, tartaric acid, malic acid, oxalic acid, glycolic acid, succinic acid, gluconic acid, glycine, acetic acid, sulfuric acid, and combinations thereof.

3. The superabsorbent according to claim 1, wherein the aluminum ions are applied in the form of an aqueous solution further comprising an addition of at least one further cation, where the cation is selected from the group consisting of alkali metal ions, alkaline earth metal ions, ammonium ions, cations of one or more transition metals or rare earth metals, and combinations thereof.

4. The superabsorbent according to claim 1, wherein the solution includes clusters having the theoretical composition $Al^{3+}{}_A(C_3H_5O_3{}^-)_{x \cdot A} S_{y \cdot A}{}^{M-}(H_2PO_4{}^-)_{Z \cdot A}(OH^-)_{(3A-x \cdot A-M \cdot y \cdot A-Z \cdot A)}$ where S is the anion of an optionally present third acid having charge M, x is a value within a range of 0.01-2.99, y is a value within a range of 0-2.8, and z is a value within a range of 0.05-2.9.

5. The superabsorbent according to claim 4, wherein the aluminum ions are applied in the form of an aqueous solution in which $(3A-x \cdot A-M \cdot y \cdot A-z \cdot A)>0$.

6. The superabsorbent according to claim 1 wherein the solution comprises not more than 5% by weight of sulfate ions.

7. The superabsorbent according to claim 1, which is surface postcrosslinked with postcrosslinkers that form covalent bonds with polar groups at a surface of the superabsorbent particles.

8. The superabsorbent according to claim 1, which has been complexed with at least 0.008% by weight and at most 0.15% by weight of aluminum, calculated in each case as the metal and based on the total amount of the anhydrous superabsorbent.

9. The superabsorbent according to claim 4, which has been complexed with at least 0.020% by weight and at most 0.05% by weight of aluminum, calculated in each case as the metal and based on the total amount of the anhydrous superabsorbent.

10. A process for producing a superabsorbent by polymerizing an aqueous monomer solution comprising
   a) at least one ethylenically unsaturated monomer which bears an acid group and is optionally at least partly in salt form,
   b) at least one crosslinker,
   c) at least one initiator,
   d) optionally one or more ethylenically unsaturated monomer copolymerizable with the monomer mentioned under a),
   e) optionally one or more water-soluble polymer,
   the process further comprising
   drying of the resulting polymer,
   optionally grinding of the dried polymer and sieving of the ground polymer,
   optionally surface postcrosslinking of the dried and optionally ground and sieved polymer, and
   adding an aqueous solution comprising aluminum ions, which comprises aluminum ions in a proportion within the range of 0.5%-15% by weight (converted to $Al^{3+}$), based on the total mass of the solution, and further comprises anions of lactic acid (lactate ions) and phosphoric acid (phosphate ions), where a molar proportion of the lactate ions is within the range of 0.01-2.99 times a molar amount of $Al^{3+}$ and a molar proportion of the phosphate ions is within the range of 0.01-2.99 times the molar amount of $Al^{3+}$.

11. The process according to claim 10, wherein the solution comprising aluminum ions comprises not more than 5% by weight of sulfate ions.

12. An article for absorption of fluids, comprising a superabsorbent defined in claim 1.

13. A process for producing articles for absorption of fluid, wherein the production of the articles comprises adding a superabsorbent defined in claim 1.

14. The superabsorbent according to claim 3 wherein the cation is selected from the group consisting of $Na^+$, $K^+$, $Ca^{2+}$, $Mg^{2+}$, $Zr^{2+}$, $NH_4{}^+$, and combinations thereof.

15. The superabsorbent according to claim 4 wherein x is the value within the range of 0.75-2.0, y is the value within the range of 0-1.25, and z is the value within the range of 0.2-1.5.

* * * * *